United States Patent
Ford et al.

(10) Patent No.: US 9,969,748 B2
(45) Date of Patent: May 15, 2018

(54) FUSED BICYCLIC HETEROAROMATIC DERIVATIVES AS KINASE INHIBITORS

(71) Applicants: UCB Biopharma SPRL, Brussels (BE); Katholieke Universiteit Leuven, K.U. Leuven R&D, Leuven (BE)

(72) Inventors: Daniel James Ford, Slough (GB); Qiuya Huang, Leuven (BE); Judi Charlotte Neuss, Slough (GB); James Thomas Reuberson, Slough (GB); Bart Vanderhoydonck, Diest (BE)

(73) Assignees: UCB Biopharma SPRL, Brussels (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 0 days. days.

(21) Appl. No.: 15/318,422

(22) PCT Filed: Jun. 11, 2015

(86) PCT No.: PCT/EP2015/063051
§ 371 (c)(1),
(2) Date: Dec. 13, 2016

(87) PCT Pub. No.: WO2015/193168
PCT Pub. Date: Dec. 23, 2015

(65) Prior Publication Data
US 2017/0129905 A1    May 11, 2017

(30) Foreign Application Priority Data

Jun. 17, 2014 (GB) .................................. 1410816.1

(51) Int. Cl.
*A61K 31/519* (2006.01)
*A01N 43/90* (2006.01)
*C07D 498/04* (2006.01)
*C07D 487/04* (2006.01)
*C07D 495/04* (2006.01)

(52) U.S. Cl.
CPC .......... *C07D 498/04* (2013.01); *A61K 31/519* (2013.01); *C07D 487/04* (2013.01); *C07D 495/04* (2013.01)

(58) Field of Classification Search
CPC .................................................. A61K 31/519
USPC ....................................................... 514/262.1
See application file for complete search history.

(56) References Cited

U.S. PATENT DOCUMENTS

2009/0041872 A1    3/2009   Edwards et al.

FOREIGN PATENT DOCUMENTS

| DE | 2121950 | * 11/1972 | ............ C07D 63/18 |
|----|---------|-----------|------------------------|
| GB | 1057612 | * 2/1967 | |
| WO | WO 2004/092123 | 10/2004 | |
| WO | WO 2008/004368 | 1/2008 | |
| WO | WO 2009/008906 | 1/2009 | |
| WO | WO 2012/041872 | 4/2012 | |
| WO | WO 2012/048222 | 4/2012 | |
| WO | WO 2013/024291 | 2/2013 | |
| WO | WO 2013/068458 | 5/2013 | |
| WO | WO 2014/039714 | 3/2014 | |

OTHER PUBLICATIONS

Peng, et. al., Journal of Combinatorial Chemistry (2007), 9(3), 431-436.*
Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
International Search Report dated Aug. 3, 2015 of PCT/EP2015/063051 filed Jun. 11, 2014, 5 pages.
Ciustea et al., Identification of Non-Nucleoside DNA Synthesis Inhibitors of Vaccinia Virus by High Throughput Screening, Journal of Medicinal Chemistry, vol. 51, No. 20, Oct. 23, 2008, pp. 6563-6570.
Sizova et al., "Pyrrolo [3,2-d] Pyrimidines, IV. Synthesis and Antibacterial and Antitumor Activity of 2,4,7-Substituted Pyrrolo [3,2-d] Pyrimidines," Pharmaceutical Chemistry Journal, vol. 16, No. 11, Nov. 1, 1982, pp. 834-838.
Steindl et al., "Pharmacophore Modeling, Docking, and Principal Component Analysis Based Clustering: Combined Computer-Assisted Approaches to Identify New Inhibitors of the Human Rhinovirus Coat Protein," Journal of Medicinal Chemistry, vol. 38, No. 20, Oct. 1, 2004, pp. 6250-6260.

* cited by examiner

*Primary Examiner* — Jeffrey H Murray
(74) *Attorney, Agent, or Firm* — McDonnell Boehnen Hulbert & Berghoff LLP

(57) ABSTRACT

A series of fused bicyclic heteroaromatic derivatives of formula (IA) or (IB), as defined herein, being selective inhibitors of phosphatidylinositol-4-kinase IIIβ (PI4KIIIβ) activity, are beneficial in the treatment and/or prevention of various human ailments, including inflammatory, autoimmune and oncological disorders; viral diseases and malaria; and organ and cell transplant rejection.

12 Claims, No Drawings

FUSED BICYCLIC HETEROAROMATIC DERIVATIVES AS KINASE INHIBITORS

This application is a US national phase of International Application No. PCT/EP2015/063051, filed Jun. 11, 2015, which claims priority to Great Britain Application No. 1410816.1, filed Jun. 17, 2014.

The present invention relates to a family of fused bicyclic heteroaromatic derivatives, and to their use in therapy. The compounds provided by the present invention are selective inhibitors of phosphatidylinositol-4-kinase IIIβ (PI4KIIIβ) activity, and are accordingly of benefit as pharmaceutical agents, especially in the treatment of adverse inflammatory, autoimmune and oncological disorders, in the treatment of viral diseases and malaria, and in the management of organ and cell transplant rejection.

In addition, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2013/034738 discloses that inhibitors of PI4KIIIβ activity are useful as medicaments for the treatment of autoimmune and inflammatory disorders, and organ and cell transplant rejection.

WO 2010/103130 describes a family of oxazolo[5,4-d]pyrimidine, thiazolo[5,4-d]-pyrimidine, thieno[2,3-d]pyrimidine and purine derivatives that are active in a range of assays, including the Mixed Lymphocyte Reaction (MLR) test, and are stated to be effective for the treatment of immune and autoimmune disorders, and organ and cell transplant rejection. WO 2011/147753 discloses the same family of compounds as having significant antiviral activity. Furthermore, WO 2012/035423 discloses the same family of compounds as having significant anticancer activity.

WO 2013/024291, WO 2013/068458, WO 2014/053581, and copending international patent application PCT/EP2013/077846 (published on 26 Jun. 2014 as WO 2014/096423) describe various series of fused pyrimidine derivatives that are stated to be of benefit as pharmaceutical agents, especially in the treatment of adverse inflammatory, autoimmune and oncological disorders, in the treatment of viral diseases, and in the management of organ and cell transplant rejection.

Inhibitors of PI4KIIIβ have been identified as molecules with an ideal activity profile for the prevention, treatment and elimination of malaria (cf. C. W. McNamara et al., *Nature*, 2013, 504, 248-253).

None of the prior art available to date, however, discloses or suggests the precise structural class of fused bicyclic heteroaromatic derivatives as provided by the present invention as having activity as PI4KIIIβ inhibitors.

The compounds of the present invention are potent and selective inhibitors of PI4KIIIβ activity, inhibiting the kinase affinity of human PI4KIIIβ ($IC_{50}$) at concentrations of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for human PI4KIIIβ relative to other human kinases.

Certain compounds in accordance with the present invention are active as inhibitors when subjected to the Mixed Lymphocyte Reaction (MLR) test. The MLR test is predictive of immunosuppression or immunomodulation. Thus, when subjected to the MLR test, certain compounds of the present invention display an $IC_{50}$ value of 10 μM or less, generally of 5 μM or less, usually of 2 μM or less, typically of 1 μM or less, suitably of 500 nM or less, ideally of 100 nM or less, and preferably of 20 nM or less (again, the skilled person will appreciate that a lower $IC_{50}$ figure denotes a more active compound).

The compounds of the invention possess notable advantages in terms of their high potency, demonstrable efficacy at lower doses, and valuable pharmacokinetic and pharmacodynamic properties (including clearance and bioavailability).

The present invention provides a compound of formula (IA) or (IB) or an N-oxide thereof, or a pharmaceutically acceptable salt or solvate thereof:

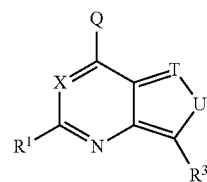

(IA)

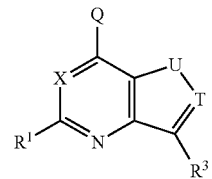

(IB)

wherein

X represents N or CH;

T represents N or C—$R^2$;

U represents oxygen, sulphur or N—$R^4$;

Q represents a group of formula (Qa), (Qb), (Qc), (Qd) or (Qe):

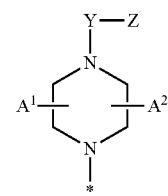

(Qa)

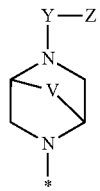

(Qb)

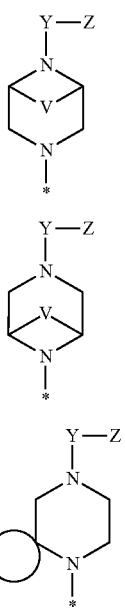

(Qc)

(Qd)

(Qe)

in which the asterisk (*) represents the point of attachment to the remainder of the molecule;

V represents —CH$_2$—, —C(CH$_3$)$_2$—, —CH$_2$CH$_2$— or —CH$_2$CH$_2$CH$_2$—;

W represents the residue of a C$_{3-7}$ cycloalkyl group;

Y represents a covalent bond, or a linker group selected from —C(O)—, —S(O)—, —S(O)$_2$—, —C(O)O—, —C(O)N(R$^5$)—, —C(O)C(O)— and —S(O)$_2$N(R$^5$)—, or a linker group of formula (Ya):

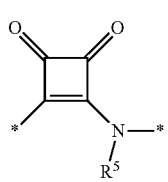

(Ya)

in which the asterisk (*) represents the point of attachment to the remainder of the molecule;

Z represents hydrogen; or Z represents C$_{1-6}$ alkyl, C$_{2-6}$ alkenyl, C$_{3-7}$ cycloalkyl, C$_{3-7}$ cycloalkyl(C$_{1-6}$)alkyl, C$_{3-7}$ heterocycloalkyl, C$_{3-7}$ heterocycloalkyl(C$_{1-6}$)alkyl, aryl, aryl(C$_{1-6}$)alkyl, heteroaryl or heteroaryl(C$_{1-6}$)alkyl, any of which groups may be optionally substituted by one or more substituents;

A$^1$ represents hydrogen, cyano or trifluoromethyl; or A$^1$ represents C$_{1-6}$ alkyl, optionally substituted by one or more substituents independently selected from fluoro, —OR$^a$, trifluoromethoxy, —NR$^b$R$^c$, —CO$_2$R$^d$ and —CONR$^b$R$^c$; or A$^1$ represents C$_{3-7}$ cycloalkyl;

A$^2$ represents hydrogen or C$_{1-6}$ alkyl;

R$^1$ and R$^2$ independently represent hydrogen, halogen, cyano, nitro, hydroxy, trifluoromethyl, trifluoromethoxy, —OR$^a$, —SR$^a$, —SOR$^a$, —SO$_2$R$^a$, —NR$^b$R$^c$, —CH$_2$NR$^b$R$^c$, —NR$^c$COR$^d$, —CH$_2$NR$^c$COR$^d$, —NR$^c$CO$_2$R$^d$, —NHCONR$^b$R$^c$, —NR$^c$SO$_2$R$^e$, —N(SO$_2$R$^e$)$_2$, —NHSO$_2$NR$^b$R$^c$, —COR$^d$, —CO$_2$R$^d$, —CONR$^b$R$^c$, —CON(OR$^a$)R$^b$ or —SO$_2$NR$^b$R$^c$; or C$_{1-6}$ alkyl, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, C$_{3-7}$ heterocycloalkenyl, heteroaryl or heteroaryl(C$_{1-6}$)alkyl, any of which groups may be optionally substituted by one or more substituents;

R$^3$ represents hydrogen, halogen or C$_{1-6}$ alkyl;

R$^4$ represents hydrogen; or R$^4$ represents C$_{1-6}$ alkyl, aryl, aryl(C$_{1-6}$)alkyl, heteroaryl or heteroaryl(C$_{1-6}$)alkyl, any of which groups may be optionally substituted by one or more substituents;

R$^5$ represents hydrogen; or R$^5$ represents C$_{1-6}$ alkyl, optionally substituted by one or more substituents independently selected from —OR$^a$ and —NR$^b$R$^c$;

R$^a$ represents hydrogen; or R$^a$ represents C$_{1-6}$ alkyl, aryl, aryl(C$_{1-6}$)alkyl, heteroaryl or heteroaryl(C$_{1-6}$)alkyl, any of which groups may be optionally substituted by one or more substituents;

R$^b$ and R$^c$ independently represent hydrogen or trifluoromethyl; or C$_{1-6}$ alkyl, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted by one or more substituents; or R$^b$ and R$^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

R$^d$ represents hydrogen; or C$_{1-6}$ alkyl, C$_{3-7}$ cycloalkyl, aryl, C$_{3-7}$ heterocycloalkyl or heteroaryl, any of which groups may be optionally substituted by one or more substituents; and R$^e$ represents C$_{1-6}$ alkyl, aryl or heteroaryl, any of which groups may be optionally substituted by one or more substituents.

Where any of the groups in the compounds of formula (IA) or (IB) above is stated to be optionally substituted, this group may be unsubstituted, or substituted by one or more substituents. Typically, such groups will be unsubstituted, or substituted by one or two substituents.

For use in medicine, the salts of the compounds of formula (IA) or (IB) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (IA) or (IB) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (IA) or (IB) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl, pentyl and hexyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Suitable $C_{2-6}$ alkenyl groups include vinyl, allyl and prop-1-en-2-yl.

Suitable $C_{3-7}$ cycloalkyl groups, which may comprise benzo-fused analogues thereof, include cyclopropyl, cyclobutyl, cyclopentyl, indanyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Suitable heterocycloalkyl groups, which may comprise benzo-fused analogues thereof, include oxetanyl, azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl and thiomorpholinyl.

Examples of suitable heterocycloalkenyl groups include oxazolinyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]pyridinyl, pyrazolyl, pyrazolo[1,5-a]pyridinyl, pyrazolo[3,4-d]pyrimidinyl, indazolyl, oxazolyl, benzoxazolyl, isoxazolyl, thiazolyl, benzothiazolyl, isothiazolyl, imidazolyl, imidazo[2,1-b]thiazolyl, benzimidazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, benzothiadiazolyl, triazolyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (IA) or (IB) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (IA) or (IB) and the formulae depicted hereinafter are intended to represent all individual stereoisomers and all possible mixtures thereof, unless stated or shown otherwise. In addition, compounds of formula (IA) or (IB) may exist as tautomers, for example keto ($CH_2C=O$) ↔ enol ($CH=CHOH$) tautomers or amide ($NHC=O$) ↔ hydroxyimine ($N=COH$) tautomers. Formula (IA) or (IB) and the formulae depicted hereinafter are intended to represent all individual tautomers and all possible mixtures thereof, unless stated or shown otherwise.

It is to be understood that each individual atom present in formula (IA) or (IB), or in the formulae depicted hereinafter, may in fact be present in the form of any of its naturally occurring isotopes, with the most abundant isotope(s) being preferred. Thus, by way of example, each individual hydrogen atom present in formula (IA) or (IB), or in the formulae depicted hereinafter, may be present as a $^1H$, $^2H$ (deuterium) or $^3H$ (tritium) atom, preferably $^1H$. Similarly, by way of example, each individual carbon atom present in formula (IA) or (IB), or in the formulae depicted hereinafter, may be present as a $^{12}C$, $^{13}C$ or $^{14}C$ atom, preferably $^{12}C$.

In one embodiment, X represents N. In another embodiment, X represents CH.

In one embodiment, T represents N. In another embodiment, T represents C—$R^2$.

In a first embodiment, U represents oxygen. In a second embodiment, U represents sulfur. In a third embodiment, U represents N—$R^4$.

In a first embodiment, T represents N and U represents oxygen or N—$R^4$. In a first aspect of that embodiment, T represents N and U represents oxygen. In a second aspect of that embodiment, T represents N and U represents N—$R^4$.

In a second embodiment, T represents C—$R^2$ and U represents sulfur or N—$R^4$. In a first aspect of that embodiment, T represents C—$R^2$ and U represents sulfur. In a second aspect of that embodiment, T represents C—$R^2$ and U represents N—$R^4$.

Selected sub-classes of compounds in accordance with the present invention include the compounds of formula (IA-1), (IA-2), (IB-1), (IB-2) and (IB-3):

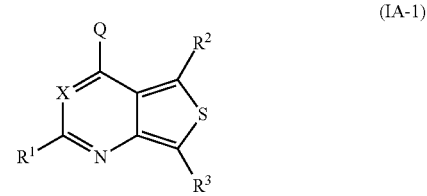

(IA-1)

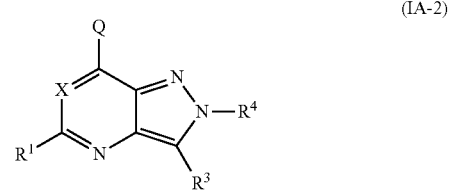

(IA-2)

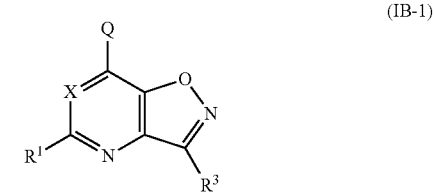

(IB-1)

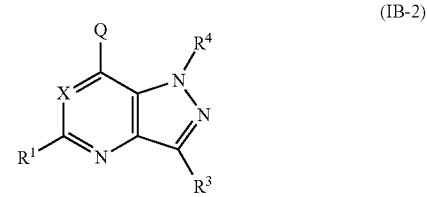

(IB-2)

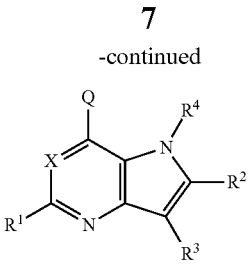
(IB-3)

wherein X, Q, R¹, R², R³ and R⁴ are as defined above.

Particular sub-classes of compounds in accordance with the present invention include the compounds of formula (IA-1), (IA-2), (IB-1) and (IB-2) as defined above.

In a first embodiment, the invention provides a compound of formula (IA-1) as defined above.

In a second embodiment, the invention provides a compound of formula (IA-2) as defined above.

In a third embodiment, the invention provides a compound of formula (IB-1) as defined above.

In a fourth embodiment, the invention provides a compound of formula (IB-2) as defined above.

In a fifth embodiment, the invention provides a compound of formula (IB-3) as defined above.

In a particular embodiment, Q represents a group of formula (Qa) as defined above. In a second embodiment, Q represents a group of formula (Qb) as defined above. In a third embodiment, Q represents a group of formula (Qc) as defined above. In a fourth embodiment, Q represents a group of formula (Qd) as defined above. In a fifth embodiment, Q represents a group of formula (Qe) as defined above.

Where Q represents a group of formula (Qa) as defined above, this may be a group of formula (Qa-1), (Qa-2), (Qa-3), (Qa-4), (Qa-5) or (Qa-6):

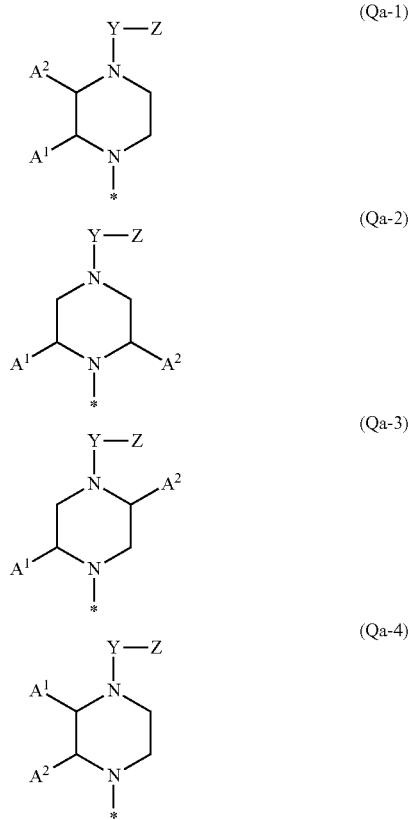

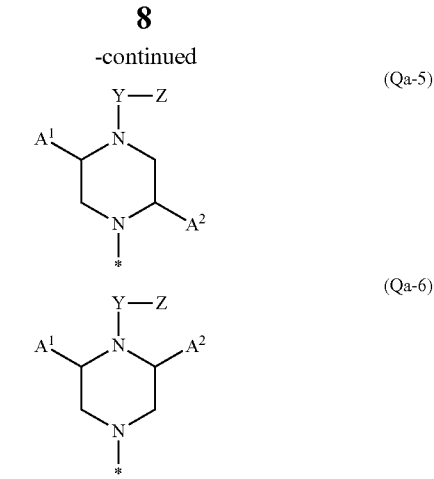

in which the asterisk (*) represents the point of attachment to the remainder of the molecule; and Y, Z, A¹ and A² are as defined above.

In a first embodiment, Q represents a group of formula (Qa-1) as defined above.

In a second embodiment, Q represents a group of formula (Qa-2) as defined above.

In a third embodiment, Q represents a group of formula (Qa-3) as defined above.

In a fourth embodiment, Q represents a group of formula (Qa-4) as defined above.

In a fifth embodiment, Q represents a group of formula (Qa-5) as defined above.

In a sixth embodiment, Q represents a group of formula (Qa-6) as defined above.

In one embodiment, V represents —CH₂— or —C(CH₃)₂—. In a first aspect of that embodiment, V represents —CH₂—. In a second aspect of that embodiment, V represents —C(CH₃)₂—. Where Q represents a group of formula (Qb) and V represents —CH₂— or —C(CH₃)₂—, the bicyclic moiety containing the integer V is a 2,5-diazabicyclo[2.2.1]-heptane ring system. Where Q represents a group of formula (Qc) or (Qd) and V represents —CH₂— or —C(CH₃)₂—, the bicyclic moiety containing the integer V is a 3,6-diazabicyclo[3.1.1]heptane ring system.

In another embodiment, V represents —CH₂CH₂—. Where Q represents a group of formula (Qb) and V represents —CH₂CH₂—, the bicyclic moiety containing the integer V is a 2,5-diazabicyclo[2.2.2]octane ring system. Where Q represents a group of formula (Qc) or (Qd) and V represents —CH₂CH₂—, the bicyclic moiety containing the integer V is a 3,8-diazabicyclo[3.2.1]octane ring system.

In a further embodiment, V represents —CH₂CH₂CH₂—. Where Q represents a group of formula (Qb) and V represents —CH₂CH₂CH₂—, the bicyclic moiety containing the integer V is a 6,8-diazabicyclo[3.2.2]nonane ring system. Where Q represents a group of formula (Qc) or (Qd) and V represents —CH₂CH₂CH₂—, the bicyclic moiety containing the integer V is a 7,9-diazabicyclo[3.3.1]nonane ring system.

Where Q represents a group of formula (Qe), the C₃₋₇ cycloalkyl group of which W is the residue is spiro-fused to the adjacent six-membered ring containing two nitrogen atoms. The cyclic group of which W is the residue is selected from cyclopropyl, cyclobutyl, cyclopentyl, cyclohexyl and cycloheptyl. Suitably, the cyclic group of which W is the residue is a C₄₋₆ cycloalkyl group. In a particular embodiment, the cyclic group of which W is the residue is cyclobutyl.

Generally, Y represents a covalent bond, or a linker group selected from —C(O)—, —S(O)—, —S(O)₂—, —C(O)

O—, —C(O)N(R$^5$)— and —S(O)$_2$N(R$^5$)—, or a linker group of formula (Ya) as defined above.

Typically, Y represents a covalent bond, or a linker group selected from —C(O)—, —C(O)O— and —C(O)N(R$^5$)—, or a linker group of formula (Ya) as defined above.

Suitably, Y represents a covalent bond, or a linker group selected from —C(O)— and —C(O)N(R$^5$)—.

Appositely, Y represents a covalent bond, or a linker group selected from —C(O)—, —S(O)—, —S(O)$_2$—, —C(O)O—, —C(O)N(R$^5$)— and —S(O)$_2$N(R$^5$)—.

Suitable values of Y include —C(O)—, —S(O)—, —S(O)$_2$—, —C(O)O—, —C(O)N(R$^5$)— and —S(O)$_2$N(R$^5$)—.

Typical values of Y include —C(O)—, —C(O)N(R$^5$)— and —C(O)C(O)—.

Selected values of Y include —C(O)— and —C(O)N(R$^5$)—.

In a first embodiment, Y represents a covalent bond. In a second embodiment, Y represents —C(O)—. In a third embodiment, Y represents —S(O)—. In a fourth embodiment, Y represents —S(O)$_2$—. In a fifth embodiment, Y represents —C(O)O—. In a sixth embodiment, Y represents —C(O)N(R$^5$)—. In a seventh embodiment, Y represents —C(O)C(O)—. In an eighth embodiment, Y represents —S(O)$_2$N(R$^5$)—. In a ninth embodiment, Y represents a group of formula (Ya) as defined above.

Generally, Z represents hydrogen; or Z represents $C_{1-6}$ alkyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents.

Appositely, Z represents $C_{1-6}$ alkyl, $C_{2-6}$ alkenyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents.

Typically, Z represents $C_{1-6}$ alkyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents.

More typically, Z represents $C_{3-7}$ cycloalkyl, $C_{3-7}$ heterocycloalkyl, aryl or heteroaryl, any of which groups may be optionally substituted by one or more substituents.

Suitably, Z represents aryl or heteroaryl, either of which groups may be optionally substituted by one or more substituents.

In a first embodiment, Z represents hydrogen. In a second embodiment, Z represents optionally substituted $C_{1-6}$ alkyl. In a third embodiment, Z represents optionally substituted $C_{2-6}$ alkenyl. In a fourth embodiment, Z represents optionally substituted $C_{3-7}$ cycloalkyl. In a fifth embodiment, Z represents optionally substituted $C_{3-7}$ cycloalkyl($C_{1-6}$)alkyl. In a sixth embodiment, Z represents optionally substituted $C_{3-7}$ heterocycloalkyl. In a seventh embodiment, Z represents optionally substituted $C_{3-7}$ heterocycloalkyl($C_{1-6}$)alkyl. In an eighth embodiment, Z represents optionally substituted aryl. In a ninth embodiment, Z represents optionally substituted aryl($C_{1-6}$)alkyl. In a tenth embodiment, Z represents optionally substituted heteroaryl. In an eleventh embodiment, Z represents optionally substituted heteroaryl($C_{1-6}$)alkyl.

In a particular embodiment, Z is other than hydrogen.

Typical values of Z include methyl, ethyl, isopropenyl, cyclopropyl, indanyl, cyclopropylmethyl, cyclopentylethyl, dihydrobenzofuranyl, pyrrolidinyl, indolinyl, dihydrobenzofuranylmethyl, morpholinylmethyl, morpholinylethyl, phenyl, benzyl, phenylethyl, furyl, benzofuryl, thienyl, indolyl, pyrazolyl, indazolyl, isoxazolyl, thiazolyl, benzothiazolyl, imidazolyl, benzimidazolyl, imidazo[1,2-a]pyridinyl, benzothiadiazolyl, pyridinyl, quinolinyl, isoquinolinyl, pyridazinyl, pyrimidinyl, pyrazinyl, quinoxalinyl, indolylmethyl, thiazolylmethyl, imidazo[2,1-b]thiazolylmethyl, pyridinylmethyl, furylethyl, benzimidazolylethyl and pyridinylethyl, any of which groups may be optionally substituted by one or more substituents.

Illustrative values of Z include phenyl, pyridinyl and pyrazinyl, any of which groups may be optionally substituted by one or more substituents.

Suitable values of Z include phenyl and pyridinyl, either of which groups may be optionally substituted by one or more substituents.

In one embodiment, Z is unsubstituted. In another embodiment, Z is substituted by one or more substituents, typically by one, two or three substituents, suitably by one or two substituents. In one aspect of that embodiment, Z is monosubstituted. In another aspect of that embodiment, Z is disubstituted. In a further aspect of that embodiment, Z is trisubstituted.

Typical examples of optional substituents on Z include one or more substituents independently selected from halogen, cyano, nitro, $C_{1-6}$ alkyl, trifluoromethyl, cyano-($C_{1-6}$) alkyl, ($C_{3-7}$)heterocycloalkyl, halo($C_{3-7}$)heterocycloalkyl, ($C_{1-6}$)alkyl($C_{3-7}$)heterocycloalkyl, ($C_{2-6}$)alkoxycarbonyl($C_{3-7}$)heterocycloalkyl, dihalo($C_{3-7}$)heterocycloalkyl, ($C_{3-7}$)heterocycloalkyl($C_{1-6}$)alkyl, ($C_{1-6}$)alkyl($C_{3-7}$)heterocycloalkyl($C_{1-6}$)alkyl, heteroaryl, hydroxy, oxo, $C_{1-6}$ alkoxy, difluoromethoxy, trifluoromethoxy, trifluoroethoxy ($C_{3-7}$) heterocycloalkoxy, ($C_{2-6}$)alkoxycarbonyl($C_{3-7}$)heterocycloalkoxy, ($C_{3-7}$)heterocycloalkyl($C_{1-6}$)alkoxy, aryloxy, haloaryloxy, ($C_{1-6}$)alkoxyaryloxy, $C_{1-3}$ alkylenedioxy, dihalo($C_{1-3}$)alkylenedioxy, arylcarbonyloxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, di($C_{1-6}$)-alkylamino($C_{1-6}$)alkyl, arylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aryloxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Selected examples of optional substituents on Z include one or more substituents independently selected from $C_{1-6}$ alkyl, trifluoromethyl, ($C_{3-7}$)heterocycloalkyl, dihalo($C_{3-7}$)heterocycloalkyl, $C_{1-6}$ alkoxy, trifluoromethoxy and di($C_{1-6}$)alkylamino.

Suitable examples of optional substituents on Z include one or more substituents independently selected from $C_{1-6}$ alkyl, dihalo($C_{3-7}$)heterocycloalkyl, $C_{1-6}$ alkoxy, trifluoromethoxy and di($C_{1-6}$)alkylamino.

Typical examples of specific substituents on Z include fluoro, chloro, bromo, cyano, nitro, methyl, ethyl, isopropyl, tert-butyl, trifluoromethyl, cyanomethyl, azetidinyl, pyrrolidinyl, piperazinyl, morpholinyl, fluoroazetidinyl, fluoropyrrolidinyl, methylpiperazinyl, tert-butoxycarbonylpiperazinyl, difluoroazetidinyl, difluoropyrrolidinyl, difluoropiperidinyl, pyrrolidinylmethyl, piperidinylmethyl, morpholinylmethyl, methyl-piperazinylmethyl, pyrazolyl, imidazolyl, hydroxy, oxo, methoxy, ethoxy, isopropoxy, difluoromethoxy, trifluoromethoxy, trifluoroethoxy, oxetanyloxy, azetidinyloxy, tetrahydrofuranyloxy, pyrrolidinyloxy, tert-butoxycarbonylazetidinyloxy, tert-butoxycarbonylpyrrolidinyloxy, tetrahydrofuranylmethoxy, morpholinylethoxy, phenoxy, chlorophenoxy, methoxyphenoxy, methylenedioxy, ethylenedioxy, difluoromethylenedioxy, benzoyloxy, methylthio, methylsulfinyl, methylsulfonyl, amino, methylamino, tert-butylamino, dimethylamino, dimethylaminomethyl, phenylamino, acetylamino, methoxycarbonylamino, methylsulfonylamino, formyl, acetyl, cyclopropylcarbonyl, azetidinylcarbonyl, pyrrolidinylcarbonyl, piperidinylcarbonyl, piperazinylcarbonyl, morpholinylcarbonyl, carboxy, methoxycarbonyl, ethoxycarbonyl, tert-butoxycarbonyl, benzyloxycarbonyl aminocarbonyl, methylaminocarbonyl, dimethylaminocarbonyl, aminosulfonyl, methylaminosulfonyl and dimethylaminosulfonyl.

Selected examples of specific substituents on Z include methyl, trifluoromethyl, azetidinyl, difluoroazetidinyl, methoxy, ethoxy, isopropoxy, trifluoromethoxy and dimethylamino.

Suitable examples of specific substituents on Z include methyl, difluoroazetidinyl, methoxy, ethoxy, trifluoromethoxy and dimethylamino.

Selected values of Z include phenoxymethyl, chlorophenoxymethyl, methoxyphenoxymethyl, tert-butoxycarbonylmethyl, benzyloxycarbonylmethyl, phenoxyethyl, isopropenyl, cyclopropyl, indanyl, cyclopropylmethyl, cyclopentylethyl, (methyl)(oxo)pyrrolidinyl, dihydrobenzofuranyl, methylindolinyl, dihydrobenzofuranylmethyl, morpholinylmethyl, morpholinylethyl, phenyl, nitrophenyl, methylphenyl, ethylphenyl, cyanomethylphenyl, morpholinylphenyl, pyrazolylphenyl, imidazolylphenyl, methoxyphenyl, difluoromethoxyphenyl, trifluoromethoxyphenyl, morpholinylethoxy-phenyl, ethylenedioxyphenyl, difluoromethylenedioxyphenyl, benzoyloxyphenyl, dimethylaminophenyl, acetylaminophenyl, aminocarbonylphenyl, (chloro)(methyl)-phenyl, dimethylphenyl, (methyl)(trifluoromethyl)phenyl, bis(trifluoromethyl)phenyl, (fluoropyrrolidinyl)(methyl)phenyl, (methyl)(pyrrolidinylmethyl)phenyl, (methyl)-(morpholinylmethyl)phenyl, (methyl) (methylpiperazinylmethyl)phenyl, (fluoro)-(methoxy) phenyl, (chloro)(methoxy)phenyl, (cyano)(methoxy)phenyl, (methoxy)-(methyl)phenyl, (methoxy)(trifluoromethyl)phenyl, dimethoxyphenyl, (difluoromethoxy)-(methyl)phenyl, (methyl)(trifluoromethoxy)phenyl, (methyl)(oxetanyloxy) phenyl, (azetidinyloxy)(methyl)phenyl, (tert-butoxycarbonylazetidinyloxy)(methyl)phenyl, (methyl)(tetrahydrofuranylmethoxy)phenyl, (methyl)(morpholinylethoxy)phenyl, (dimethylaminomethyl)(methyl)phenyl, trimethoxyphenyl, benzyl, cyanobenzyl, methylbenzyl, methoxybenzyl, methylenedioxybenzyl, dimethylaminobenzyl, dimethoxy-benzyl, phenylethyl, fluorophenylethyl, methylphenylethyl, (hydroxy)(phenyl)ethyl, methoxyphenylethyl, methylfuryl, methoxybenzofuryl, thienyl, indolyl, methylindolyl, pyrazolyl, methylpyrazolyl, dimethylpyrazolyl, indazolyl, methylindazolyl, dimethyl-isoxazolyl, thiazolyl, methylthiazolyl, tert-butylthiazolyl, ethoxycarbonylthiazolyl, benzothiazolyl, methoxybenzothiazolyl, methylimidazolyl, benzimidazolyl, methyl-benzimidazolyl, trifluoromethylbenzimidazolyl, piperidinylmethylbenzimidazolyl, morpholinylmethylbenzimidazolyl, imidazo[1,2-a]pyridinyl, benzothiadiazolyl, pyridinyl, chloropyridinyl, methylpiperazinylpyridinyl, methoxypyridinyl, dimethylpyridinyl, (methyl)(trifluoromethyl)pyridinyl, (azetidinyl)(methyl)pyridinyl, (methyl)(pyrrolidinyl)-pyridinyl, (methyl)(piperazinyl)pyridinyl, (fluoroazetidinyl)(methyl)pyridinyl, (fluoropyrrolidinyl)(methyl)pyridinyl, (methyl)(methylpiperazinyl)pyridinyl, (tert-butoxycarbonylpiperazinyl)(methyl)pyridinyl, (difluoroazetidinyl)(methyl)pyridinyl, (difluoropyrrolidinyl)(methyl) pyridinyl, (difluoropiperidinyl)(methyl)pyridinyl, (methyl)-(pyrrolidinylmethyl)pyridinyl, (methyl)(morpholinylmethyl)pyridinyl, (methyl)(methylpiperazinylmethyl)pyridinyl, (hydroxy)(methyl)pyridinyl, (dimethyl)(oxo)pyridinyl, (chloro)(methoxy)pyridinyl, (methoxy)(methyl)pyridinyl, (methoxy)(trifluoromethyl)-pyridinyl, dimethoxypyridinyl, (ethoxy)(methyl)pyridinyl, (isopropoxy)(methyl)pyridinyl, (difluoromethoxy)(methyl) pyridinyl, (methyl)(trifluoroethoxy)pyridinyl, (methyl)-(tetrahydrofuranyloxy)pyridinyl, (methyl)(pyrrolidinyloxy) pyridinyl, (tert-butoxy-carbonylazetidinyloxy)(methyl) pyridinyl, (tert-butoxycarbonylpyrrolidinyloxy)(methyl)-pyridinyl, (methyl)(methylamino)pyridinyl, (dimethylamino)(methyl)pyridinyl, quinolinyl, isoquinolinyl, methoxypyridazinyl, pyrimidinyl, (difluoroazetidinyl) (methyl)-pyrimidinyl, methoxypyrimidinyl, (methoxy)(methyl)pyrimidinyl, (dimethylamino)-(methyl)pyrimidinyl, pyrazinyl, methoxypyrazinyl, (methoxy)(methyl)pyrazinyl, quinoxalinyl, indolylmethyl, thiazolylmethyl, methylthiazolylmethyl, imidazo[2,1-b]-thiazolylmethyl, pyridinylmethyl, furylethyl, benzimidazolylethyl and pyridinylethyl. Additional values include (isopropoxy)(methyl)phenyl and (dimethylamino)(methyl)-pyrazinyl.

Representative values of Z include methoxyphenyl, dimethylaminophenyl, (methoxy)(methyl)phenyl, (isopropoxy)(methyl)phenyl, (methyl)(trifluoromethoxy)-phenyl, (azetidinyl)(methyl)pyridinyl, (difluoroazetidinyl)(methyl) pyridinyl, (methoxy)-(trifluoromethyl)pyridinyl, dimethoxypyridinyl, (ethoxy)(methyl)pyridinyl, (dimethylamino)(methyl)pyridinyl and (dimethylamino)(methyl) pyrazinyl.

Typical values of Z include methoxyphenyl, dimethylaminophenyl, (methoxy)(methyl)phenyl, (methyl)(trifluoromethoxy)phenyl, (difluoroazetidinyl)-(methyl)pyridinyl, dimethoxypyridinyl and (ethoxy)(methyl)pyridinyl.

In a first embodiment, Z represents methoxyphenyl, especially 4-methoxyphenyl.

In a second embodiment, Z represents dimethylaminophenyl, especially 4-(dimethylamino)phenyl.

In a third embodiment, Z represents (methoxy)(methyl) phenyl. In a first aspect of that embodiment, Z represents 4-methoxy-2-methylphenyl. In a second aspect of that embodiment, Z represents 4-methoxy-3-methylphenyl.

In a fourth embodiment, Z represents (difluoromethoxy)(methyl)phenyl, especially 4-(difluoromethoxy)-2-methylphenyl.

In a fifth embodiment, Z represents (methyl)(trifluoromethoxy)phenyl, especially 2-methyl-4-(trifluoromethoxy)phenyl.

In a sixth embodiment, Z represents imidazo[1,2-a]pyridinyl, especially imidazo-[1,2-a]pyridin-8-yl.

In a seventh embodiment, Z represents (difluoroazetidinyl)(methyl)pyridinyl, especially 6-(3,3-difluoroazetidin-1-yl)-2-methylpyridin-3-yl.

In an eighth embodiment, Z represents (methoxy)(methyl) pyridinyl. In a first aspect of that embodiment, Z represents 6-methoxy-2-methylpyridin-3-yl. In a second aspect of that embodiment, Z represents 6-methoxy-5-methylpyridin-3-yl.

In a ninth embodiment, Z represents dimethoxypyridinyl, especially 2,6-dimethoxypyridin-3-yl.

In a tenth embodiment, Z represents (ethoxy)(methyl) pyridinyl, especially 6-ethoxy-2-methylpyridin-3-yl.

In an eleventh embodiment, Z represents (isopropoxy)(methyl)pyridinyl, especially 6-isopropoxy-2-methylpyridin-3-yl.

In a twelfth embodiment, Z represents (difluoromethoxy)(methyl)pyridinyl, especially 6-(difluoromethoxy)-2-methylpyridin-3-yl.

In a thirteenth embodiment, Z represents (isopropoxy)(methyl)phenyl, especially 4-isopropoxy-2-methylphenyl.

In a fourteenth embodiment, Z represents (azetidinyl)(methyl)pyridinyl, especially 6-(azetidin-1-yl)-2-methylpyridin-3-yl.

In a fifteenth embodiment, Z represents (methoxy)(trifluoromethyl)pyridinyl, especially 5-methoxy-6-(trifluoromethyl)pyridin-2-yl.

In a sixteenth embodiment, Z represents (dimethylamino)(methyl)pyridinyl, especially 6-(dimethylamino)-2-methylpyridin-3-yl.

In a seventeenth embodiment, Z represents (dimethylamino)(methyl)pyrazinyl, especially 5-(dimethylamino)-3-methylpyrazin-2-yl.

Generally, $A^1$ represents hydrogen, cyano or trifluoromethyl; or $A^1$ represents $C_{1-6}$ alkyl, optionally substituted by one or more substituents independently selected from —$OR^a$, —$NR^bR^c$, —$CO_2R^d$ and —$CONR^bR^c$; or $A^1$ represents $C_{3-7}$ cycloalkyl.

Typically, $A^1$ represents hydrogen or cyano; or $A^1$ represents $C_{1-6}$ alkyl, optionally substituted by one or more substituents independently selected from —$OR^a$, —$CO_2R^d$ and —$CONR^bR^c$; or $A^1$ represents $C_{3-7}$ cycloalkyl.

Suitably, $A^1$ represents hydrogen; or $A^1$ represents $C_{1-6}$ alkyl, optionally substituted by —$OR^a$.

Appositely, $A^1$ represents hydrogen or $C_{1-6}$ alkyl.

In a first embodiment, $A^1$ represents hydrogen. In a second embodiment, $A^1$ represents cyano. In a third embodiment, $A^1$ represents trifluoromethyl. In a fourth embodiment, $A^1$ represents $C_{1-6}$ alkyl, optionally substituted by one or more substituents independently selected from fluoro, —$OR^a$, trifluoromethoxy, —$NR^bR^c$, —$CO_2R^d$ and —$CONR^bR^c$. In a first aspect of that embodiment, $A^1$ represents $C_{1-6}$ alkyl, optionally substituted by one or more substituents independently selected from —$OR^a$, —$NR^bR^c$, —$CO_2R^d$ and —$CONR^bR^c$. In a second aspect of that embodiment, $A^1$ represents $C_{1-6}$ alkyl, optionally substituted by one or more substituents independently selected from —$OR^a$, —$CO_2R^d$ and —$CONR^bR^c$. In a third aspect of that embodiment, $A^1$ represents $C_{1-6}$ alkyl, optionally substituted by one or more substituents independently selected from —$OR^a$ and —$NR^bR^c$. In a fourth aspect of that embodiment, $A^1$ represents unsubstituted $C_{1-6}$ alkyl, typically methyl, ethyl, isopropyl or isobutyl, especially methyl or ethyl. In a fifth aspect of that embodiment, $A^1$ represents $C_{1-6}$ alkyl monosubstituted by —$OR^a$, —$CO_2R^d$ or —$CONR^bR^c$. In a sixth aspect of that embodiment, $A^1$ represents $C_{1-6}$ alkyl monosubstituted by —$OR^a$ or —$NR^bR^c$. In a seventh aspect of that embodiment, $A^1$ represents $C_{1-6}$ alkyl monosubstituted by —$OR^a$, especially hydroxyethyl. In an eighth aspect of that embodiment, $A^1$ represents $C_{1-6}$ alkyl disubstituted by two substituents independently selected from —$OR^a$ and —$NR^bR^c$. In a fifth embodiment, $A^1$ represents $C_{3-7}$ cycloalkyl, especially cyclopropyl.

Selected values of $A^1$ include hydrogen, cyano, methyl, ethyl, isopropyl, isobutyl, —$CH_2OR^a$, —$CH_2CH_2OR^a$, —$CH_2CO_2R^d$, —$CH_2CONR^bR^c$ and cyclopropyl.

Illustrative values of $A^1$ include hydrogen, methyl, ethyl and —$CH_2CH_2OR^a$.

Particular values of $A^1$ include hydrogen, methyl, ethyl and hydroxyethyl.

Apposite values of $A^1$ include hydrogen, methyl and ethyl.

A first particular value of $A^1$ is hydrogen.
A second particular value of $A^1$ is methyl.
A third particular value of $A^1$ is ethyl.
A fourth particular value of $A^1$ is hydroxyethyl, especially 2-hydroxyethyl.

In a particular embodiment, $A^2$ represents hydrogen. In another embodiment, $A^2$ represents $C_{1-6}$ alkyl, especially methyl.

Selected values of $A^2$ include hydrogen and methyl.

Suitably, $R^1$ represents hydrogen, halogen, cyano, nitro, hydroxy, trifluoromethyl, trifluoromethoxy, —$OR^a$, —$SO_2R^a$, —$NR^bR^c$, —$CH_2NR^bR^c$, —$NR^cCOR^d$, —$CH_2NR^cCOR^d$, —$NR^cCO_2R^d$, —$NHCONR^bR^c$, —$NR^cSO_2R^e$, —$NHSO_2NR^bR^c$, —$COR^d$, —$CO_2R^d$, —$CONR^bR^c$, —$CON(OR^a)R^b$ or —$SO_2NR^bR^c$; or $R^1$ represents $C_{1-6}$ alkyl, aryl or heteroaryl, any of which groups may be optionally substituted by one or more substituents.

Typically, $R^1$ represents hydrogen, —$NR^bR^c$ or —$NR^cCOR^d$; or $R^1$ represents $C_{1-6}$ alkyl, which group may be optionally substituted by one or more substituents.

Suitable values of $R^1$ include hydrogen and —$NR^bR^c$.

In a first embodiment, $R^1$ represents hydrogen. In a second embodiment, $R^1$ represents cyano. In a third embodiment, $R^1$ represents —$OR^a$. In a fourth embodiment, $R^1$ represents —$SR^a$. In a fifth embodiment, $R^1$ represents —$SO_2R^a$. In a sixth embodiment, $R^1$ represents —$NR^bR^c$. In a seventh embodiment, $R^1$ represents —$NR^cCOR^d$. In an eighth embodiment, $R^1$ represents optionally substituted $C_{1-6}$ alkyl. In one aspect of that embodiment, $R^1$ represents optionally substituted methyl.

Examples of typical substituents on $R^1$ include one or more substituents independently selected from halogen, cyano, nitro, $C_{1-6}$ alkyl, trifluoromethyl, aryl($C_{1-6}$)alkyl, hydroxy, $C_{1-6}$ alkoxy, difluoromethoxy, trifluoromethoxy, aryloxy, $C_{1-4}$ alkylenedioxy, $C_{1-6}$ alkoxy($C_{1-6}$)alkyl, $C_{1-6}$ alkylthio, $C_{1-6}$ alkylsulphonyl, oxo, amino, $C_{1-6}$ alkylamino, di($C_{1-6}$)alkylamino, $C_{2-6}$ alkylcarbonylamino, $C_{2-6}$ alkoxycarbonylamino, aryl($C_{1-6}$)alkoxycarbonylamino, $C_{1-6}$ alkylaminocarbonylamino, arylaminocarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl and di($C_{1-6}$)alkylaminosulphonyl.

Specific examples of typical substituents on $R^1$ include one or more substituents independently selected from fluoro, chloro, bromo, cyano, nitro, methyl, ethyl, tert-butyl, trifluoromethyl, benzyl, hydroxy, methoxy, difluoromethoxy, trifluoromethoxy, phenoxy, methylenedioxy, ethylenedioxy, methoxymethyl, methylthio, methylsulphonyl, oxo, amino, methylamino, dimethylamino, acetylamino, methoxycarbonylamino, ethoxycarbonylamino, benzyloxycarbonylamino, ethylaminocarbonylamino, butylaminocarbonylamino, phenylaminocarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl.

Generally, $R^2$ represents hydrogen, cyano, hydroxy, trifluoromethyl, —$NR^cCO_2R^d$, —$COR^d$, —$CO_2R^d$, —$CONR^bR^c$ or —$CON(OR^a)R^b$; or $R^2$ represents $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents.

Typically, $R^2$ represents hydrogen, —$CO_2R^d$, —$CONR^bR^c$ or —$CON(OR^a)R^b$; or $R^2$ represents $C_{3-7}$ heterocycloalkenyl, which group may be optionally substituted by one or more substituents.

In a first embodiment, $R^2$ represents hydrogen. In a second embodiment, $R^2$ represents cyano. In a third embodiment, $R^2$ represents hydroxy. In a fourth embodiment, $R^2$ represents trifluoromethyl. In a fifth embodiment, $R^2$ represents —$NR^cCO_2R^d$. In a sixth embodiment, $R^2$ represents —$COR^d$. In a seventh embodiment, $R^2$ represents —$CO_2R^d$.

In an eighth embodiment, $R^2$ represents —CONR$^b$R$^c$. In a ninth embodiment, $R^2$ represents —CON(OR$^a$)R$^b$. In a tenth embodiment, $R^2$ represents optionally substituted $C_{1-6}$ alkyl. In a first aspect of that embodiment, $R^2$ represents unsubstituted $C_{1-6}$ alkyl. In a second aspect of that embodiment, $R^2$ represents monosubstituted $C_{1-6}$ alkyl. In a third aspect of that embodiment, $R^2$ represents disubstituted $C_{1-6}$ alkyl. In an eleventh embodiment, $R^2$ represents optionally substituted $C_{3-7}$ cycloalkyl. In a first aspect of that embodiment, $R^2$ represents unsubstituted $C_{3-7}$ cycloalkyl. In a second aspect of that embodiment, $R^2$ represents monosubstituted $C_{3-7}$ cycloalkyl. In a third aspect of that embodiment, $R^2$ represents disubstituted $C_{3-7}$ cycloalkyl. In a twelfth embodiment, $R^2$ represents optionally substituted aryl. In a first aspect of that embodiment, $R^2$ represents unsubstituted aryl. In a second aspect of that embodiment, $R^2$ represents monosubstituted aryl. In a third aspect of that embodiment, $R^2$ represents disubstituted aryl. In a thirteenth embodiment, $R^2$ represents optionally substituted $C_{3-7}$ heterocycloalkyl. In a first aspect of that embodiment, $R^2$ represents unsubstituted $C_{3-7}$ heterocycloalkyl. In a second aspect of that embodiment, $R^2$ represents monosubstituted $C_{3-7}$ heterocycloalkyl. In a third aspect of that embodiment, $R^2$ represents disubstituted $C_{3-7}$ heterocycloalkyl. In a fourteenth embodiment, $R^2$ represents optionally substituted $C_{3-7}$ heterocycloalkenyl. In a first aspect of that embodiment, $R^2$ represents unsubstituted $C_{3-7}$ heterocycloalkenyl. In a second aspect of that embodiment, $R^2$ represents monosubstituted $C_{3-7}$ heterocycloalkenyl. In a third aspect of that embodiment, $R^2$ represents disubstituted $C_{3-7}$ heterocycloalkenyl. In a fifteenth embodiment, $R^2$ represents optionally substituted heteroaryl. In a first aspect of that embodiment, $R^2$ represents unsubstituted heteroaryl. In a second aspect of that embodiment, $R^2$ represents monosubstituted heteroaryl. In a third aspect of that embodiment, $R^2$ represents disubstituted heteroaryl.

Where $R^2$ represents optionally substituted $C_{1-6}$ alkyl, suitable values include methyl, ethyl, n-propyl, isopropyl, n-butyl, isobutyl and tert-butyl, any of which groups may be optionally substituted by one or more substituents. Selected values include methyl, hydroxymethyl, chloropropyl and isobutyl. Particular values include methyl and isobutyl, especially methyl.

Where $R^2$ represents optionally substituted $C_{3-7}$ cycloalkyl, a suitable value is cyclohexyl, optionally substituted by one or more substituents.

Where $R^2$ represents optionally substituted aryl, a suitable value is phenyl, optionally substituted by one or more substituents. Selected values include phenyl, fluorophenyl, chlorophenyl and methoxyphenyl.

Where $R^2$ represents optionally substituted $C_{3-7}$ heterocycloalkyl, typical values include azetidinyl, pyrrolidinyl, piperidinyl, piperazinyl, morpholinyl and thiomorpholinyl, any of which groups may be optionally substituted by one or more substituents.

Where $R^2$ represents optionally substituted $C_{3-7}$ heterocycloalkenyl, a typical value is oxazolinyl, optionally substituted by one or more substituents. Suitable values include oxazolinyl, methyloxazolinyl, isopropyloxazolinyl and dimethyloxazolinyl.

Where $R^2$ represents optionally substituted heteroaryl, typical values include pyrrolyl, furyl, thienyl, imidazolyl, oxazolyl, isoxazolyl, thiazolyl, isothiazolyl, pyrazolyl, triazolyl, oxadiazolyl, thiadiazolyl, pyridinyl, pyrimidinyl, pyridazinyl, pyrazinyl, tetrazolyl and triazinyl, any of which groups may be optionally substituted by one or more substituents. Suitable values include oxadiazolyl and pyridinyl, either of which groups may be optionally substituted by one or more substituents. Selected values include methyloxadiazolyl, isopropyloxadiazolyl, tert-butyloxadiazolyl and pyridinyl.

In a selected embodiment, $R^2$ represents hydrogen, cyano, hydroxy, trifluoromethyl, —NR$^c$CO$_2$R$^d$, —COR$^d$, —CO$_2$R$^d$, —CONR$^b$R$^c$ or —CON(OR$^a$)R$^b$; or $R^2$ represents $C_{1-6}$ alkyl, cyclohexyl, phenyl, oxazolinyl, oxadiazolyl or pyridinyl, any of which groups may be optionally substituted by one or more substituents.

In a typical embodiment, $R^2$ represents hydrogen, —CO$_2$R$^d$, —CONR$^b$R$^c$ or —CON(OR$^a$)R$^b$; or $R^2$ represents oxazolinyl, which group may be optionally substituted by one or more substituents.

Typical examples of optional substituents on $R^2$ include one or more substituents independently selected from halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$) alkylaminosulfonyl.

Typical examples of specific substituents on $R^2$ include one or more substituents independently selected from fluoro, chloro, bromo, cyano, nitro, methyl, ethyl, isopropyl, tert-butyl, trifluoromethyl, hydroxy, methoxy, isopropoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, aminocarbonyl, methylaminocarbonyl, dimethylaminocarbonyl, aminosulfonyl, methylaminosulfonyl and dimethylaminosulfonyl.

Typical values of $R^2$ include hydrogen, cyano, hydroxy, trifluoromethyl, —NR$^c$CO$_2$R$^d$, —COR$^d$, —CO$_2$R$^d$, —CONR$^b$R$^c$, —CON(OR$^a$)R$^b$, methyl, hydroxymethyl, chloropropyl, isobutyl, cyclohexyl, phenyl, fluorophenyl, chlorophenyl, methoxyphenyl, oxazolinyl, methyloxazolinyl, isopropyloxazolinyl, dimethyloxazolinyl, methyloxadiazolyl, isopropyloxadiazolyl, tert-butyloxadiazolyl and pyridinyl.

Suitable values of $R^2$ include hydrogen, —CO$_2$R$^d$, —CONR$^b$R$^c$, —CON(OR$^a$)R$^b$ and oxazolinyl.

Typically, $R^3$ represents hydrogen or $C_{1-6}$ alkyl.

In a first embodiment, $R^3$ represents hydrogen. In a second embodiment, $R^3$ represents halogen, especially fluoro or chloro. In a first aspect of that embodiment, $R^3$ represents fluoro. In a second aspect of that embodiment, $R^3$ represents chloro. In a third embodiment, $R^3$ represents $C_{1-6}$ alkyl, especially methyl.

Typical values of $R^3$ include hydrogen and methyl.

Typically, $R^4$ represents hydrogen; or $R^4$ represents $C_{1-6}$ alkyl, aryl or heteroaryl, any of which groups may be optionally substituted by one or more substituents.

Suitably, $R^4$ represents hydrogen; or $R^4$ represents $C_{1-6}$ alkyl, which group may be optionally substituted by one or more substituents.

In a first embodiment, $R^4$ represents hydrogen. In a second embodiment, $R^4$ represents optionally substituted $C_{1-6}$ alkyl. In a first aspect of that embodiment, $R^4$ represents unsubstituted $C_{1-6}$ alkyl. In a second aspect of that embodiment, $R^4$ represents monosubstituted $C_{1-6}$ alkyl. In a third aspect of that embodiment, $R^4$ represents disubstituted $C_{1-6}$ alkyl. In a third embodiment, $R^4$ represents optionally substituted aryl. In a first aspect of that embodiment, $R^4$ represents unsubstituted aryl. In a second aspect of that embodiment, $R^4$ represents monosubstituted aryl. In a third aspect of that embodiment, $R^4$ represents disubstituted aryl. In a fourth embodiment, $R^4$ represents optionally substituted aryl($C_{1-6}$)alkyl. In a first aspect of that embodiment, $R^4$ represents unsubstituted aryl($C_{1-6}$)alkyl. In a second aspect of that embodiment, $R^4$ represents monosubstituted aryl ($C_{1-6}$)alkyl. In a third aspect of that embodiment, $R^4$ represents disubstituted aryl($C_{1-6}$)alkyl. In a fifth embodiment, $R^4$ represents optionally substituted heteroaryl. In a first aspect of that embodiment, $R^4$ represents unsubstituted heteroaryl. In a second aspect of that embodiment, $R^4$ represents monosubstituted heteroaryl. In a third aspect of that embodiment, $R^4$ represents disubstituted heteroaryl. In a sixth embodiment, $R^4$ represents optionally substituted heteroaryl($C_{1-6}$)alkyl. In a first aspect of that embodiment, $R^4$ represents unsubstituted heteroaryl($C_{1-6}$)alkyl. In a second aspect of that embodiment, $R^4$ represents monosubstituted heteroaryl ($C_{1-6}$)alkyl. In a third aspect of that embodiment, $R^4$ represents disubstituted heteroaryl($C_{1-6}$)alkyl.

Where $R^4$ represents optionally substituted $C_{1-6}$ alkyl, suitable values include methyl, ethyl, n-propyl, isopropyl, n-butyl, isobutyl and tert-butyl, any of which groups may be optionally substituted by one or more substituents. Selected values include methyl, ethyl, n-propyl, isopropyl and isobutyl, especially methyl.

Where $R^4$ represents optionally substituted aryl, a suitable value is phenyl, optionally substituted by one or more substituents. Selected values include phenyl, fluorophenyl, chlorophenyl and methoxyphenyl. A particular value is fluorophenyl.

Where $R^4$ represents optionally substituted aryl($C_{1-6}$) alkyl, a suitable value is benzyl, optionally substituted by one or more substituents. Selected values include benzyl, fluorobenzyl, chlorobenzyl and methoxybenzyl. A particular value is fluorobenzyl.

Where $R^4$ represents optionally substituted heteroaryl, typical values include pyrrolyl, furyl, thienyl, imidazolyl, oxazolyl, isoxazolyl, thiazolyl, isothiazolyl, pyrazolyl, triazolyl, oxadiazolyl, thiadiazolyl, pyridinyl, pyrimidinyl, pyridazinyl, pyrazinyl, tetrazolyl and triazinyl, any of which groups may be optionally substituted by one or more substituents. Suitable values include oxadiazolyl and pyridinyl, either of which groups may be optionally substituted by one or more substituents. Selected values include methyloxadiazolyl, isopropyloxadiazolyl, tert-butyloxadiazolyl and pyridinyl.

Where $R^4$ represents optionally substituted heteroaryl ($C_{1-6}$)alkyl, a suitable value is pyridinylmethyl, optionally substituted by one or more substituents.

In a typical embodiment, $R^4$ represents hydrogen; or $R^4$ represents $C_{1-6}$ alkyl, phenyl, benzyl, oxadiazolyl, pyridinyl or pyridinylmethyl, any of which groups may be optionally substituted by one or more substituents.

In a suitable embodiment, $R^4$ represents hydrogen; or $R^4$ represents $C_{1-6}$ alkyl or phenyl, either of which groups may be optionally substituted by one or more substituents.

In a selected embodiment, $R^4$ represents hydrogen; or $R^4$ represents $C_{1-6}$ alkyl, which group may be optionally substituted by one or more substituents.

Typical examples of optional substituents on $R^4$ include one or more substituents independently selected from halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$) alkylaminosulfonyl.

Typical examples of specific substituents on $R^4$ include one or more substituents independently selected from fluoro, chloro, bromo, cyano, nitro, methyl, ethyl, isopropyl, tert-butyl, trifluoromethyl, hydroxy, methoxy, isopropoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, aminocarbonyl, methylaminocarbonyl, dimethylaminocarbonyl, aminosulfonyl, methylaminosulfonyl and dimethylaminosulfonyl.

Typical values of $R^4$ include hydrogen, methyl, phenyl, fluorophenyl, chlorophenyl, methoxyphenyl, benzyl, methyloxadiazolyl, isopropyloxadiazolyl, tert-butyloxadiazolyl, pyridinyl and pyridinylmethyl.

Suitably, $R^4$ represents hydrogen or $C_{1-6}$ alkyl.

In one embodiment, $R^4$ represents hydrogen. In another embodiment, $R^4$ represents $C_{1-6}$ alkyl, especially methyl.

Appositely, $R^4$ represents methyl.

Suitably, $R^5$ represents hydrogen or $C_{1-6}$ alkyl.

Suitable values of $R^5$ include hydrogen and methyl.

In one embodiment, $R^5$ represents hydrogen. In another embodiment, $R^5$ represents $C_{1-6}$ alkyl, optionally substituted by one or more substituents independently selected from —$OR^a$ and —$NR^bR^c$. In one aspect of that embodiment, $R^5$ represents unsubstituted $C_{1-6}$ alkyl, especially methyl. In another aspect of that embodiment, $R^5$ represents $C_{1-6}$ alkyl monosubstituted by —$OR^a$ or —$NR^bR^c$. In a further aspect of that embodiment, $R^5$ represents $C_{1-6}$ alkyl disubstituted by two substituents independently selected from —$OR^a$ and —$NR^bR^c$.

Typical examples of suitable substituents on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, acetylaminomethyl, tert-butoxycarbonylamino, methylsulphonylamino, aminocarbonyl, methylaminocarbonyl and dimethylaminocarbonyl.

Typically, $R^a$ represents hydrogen; or $R^a$ represents $C_{1-6}$ alkyl, aryl($C_{1-6}$)alkyl or heteroaryl($C_{1-6}$)alkyl, any of which groups may be optionally substituted by one or more substituents.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Apposite values of $R^a$ include hydrogen; and methyl, ethyl, benzyl or isoindolylpropyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents hydrogen. In another embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$) alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolylpropyl.

Appositely, $R^a$ represents hydrogen or $C_{1-6}$ alkyl.

Individual values of $R^a$ include hydrogen and methyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$)alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tert-butoxycarbonylpyrrolidinyl and morpholinylpropyl.

Apposite values of $R^b$ include hydrogen and methyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl or ethyl, particularly methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxothiazolidinyl.

Selected examples of specific values for $R^d$ include hydrogen, methyl, ethyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Appositely, $R^d$ represents hydrogen or $C_{1-6}$ alkyl.

Individual values of $R^d$ include hydrogen, methyl and ethyl.

A particular value of $R^d$ is ethyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

One sub-class of compounds according to the invention is represented by the compounds of formula (IIA-1) or (IIB-1), and pharmaceutically acceptable salts and solvates thereof:

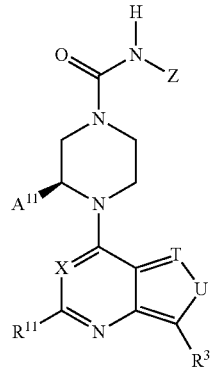
(IIA-1)

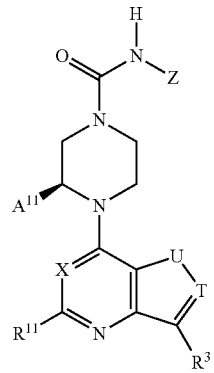
(IIB-1)

wherein
$A^{11}$ represents hydrogen, cyano, $C_{1-6}$ alkyl, —$CH_2OR^a$, —$CH_2CH_2OR^a$, —$CH_2CO_2R^d$, —$CH_2CONR^bR^c$ or $C_{3-7}$ cycloalkyl;
$R^{11}$ represents hydrogen or amino; and
X, T, U, Z, $R^3$, $R^a$, $R^b$, $R^c$ and $R^d$ are as defined above.

Appositely, $A^{11}$ represents hydrogen or $C_{1-6}$ alkyl.

In a first embodiment, $A^{11}$ represents hydrogen. In a second embodiment, $A^{11}$ represents cyano. In a third embodiment, $A^{11}$ represents $C_{1-6}$ alkyl, typically methyl, ethyl, isopropyl or isobutyl, especially methyl or ethyl. In a fourth embodiment, $A^{11}$ represents —$CH_2OR^a$. In a fifth embodiment, $A^{11}$ represents —$CH_2CH_2OR^a$. In a sixth embodiment, $A^{11}$ represents —$CH_2CO_2R^d$. In a seventh embodiment, $A^{11}$ represents —$CH_2CONR^bR^c$. In an eighth embodiment, $A^{11}$ represents $C_{3-7}$ cycloalkyl, especially cyclopropyl.

Selected values of $A^{11}$ include hydrogen, cyano, methyl, ethyl, isopropyl, isobutyl, —$CH_2OR^a$, —$CH_2CH_2OR^a$, —$CH_2CO_2R^d$, —$CH_2CONR^bR^c$ and cyclopropyl.

Illustrative values of $A^{11}$ include hydrogen, methyl, ethyl and —$CH_2CH_2OR^a$.

Particular values of $A^{11}$ include hydrogen, methyl, ethyl and 2-hydroxyethyl.

Apposite values of $A^{11}$ include hydrogen, methyl and ethyl.

A first particular value of $A^{11}$ is hydrogen.
A second particular value of $A^{11}$ is methyl.
A third particular value of $A^{11}$ is ethyl.
A fourth particular value of $A^{11}$ is 2-hydroxyethyl.

In a first embodiment, $R^{11}$ is hydrogen. In a second embodiment, $R^{11}$ is —$NH_2$.

Another sub-class of compounds according to the invention is represented by the compounds of formula (IIA-2) or (IIB-2), and pharmaceutically acceptable salts and solvates thereof:

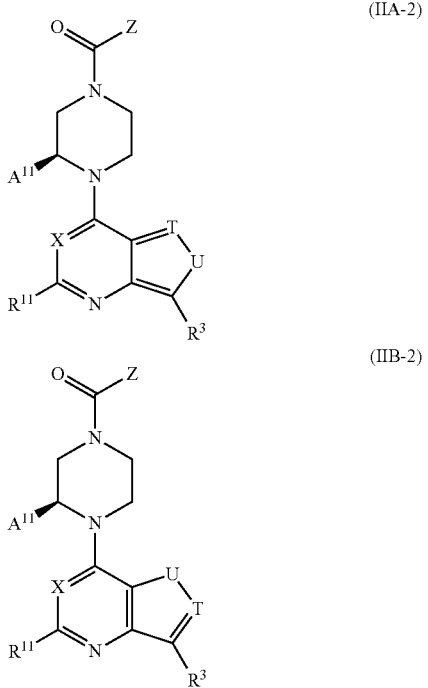

wherein X, T, U, Z, $A^{11}$, $R^3$ and $R^{11}$ are as defined above.

Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments. These include inflammatory, autoimmune and oncological disorders; viral diseases and malaria; and organ and cell transplant rejection.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, vasculitis, polymyositis, scleroderma, multiple sclerosis, ankylosing spondylitis, rheumatoid arthritis and Sjögren's syndrome. Autoimmune endocrine disorders include thyroiditis. Organ-specific autoimmune disorders include Addison's disease, haemolytic or pernicious anaemia, glomerulonephritis (including Goodpasture's syndrome), Graves' disease, idiopathic thrombocytopenic purpura, insulin-dependent diabetes mellitus, juvenile diabetes, uveitis, inflammatory bowel disease (including Crohn's disease and ulcerative colitis), pemphigus, atopic dermatitis, autoimmune hepatitis, primary biliary cirrhosis, autoimmune pneumonitis, autoimmune carditis, myasthenia gravis and spontaneous infertility.

Oncological disorders, which may be acute or chronic, include proliferative disorders, especially cancer, in animals, including mammals, especially humans. Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle.

Viral diseases include infections caused by various families of virus, including the Retroviridae, Flaviviridae, Picornaviridae. Various genera within the Retroviridae family include *Alpharetrovirus, Betaretrovirus, Gammaretrovirus, Deltaretrovirus, Epsilonretrovirus, Lentivirus* and *Spumavirus*. Members of the *Lentivirus* genus include human immunodeficiency virus 1 (HIV-1) and human immunodeficiency virus 2 (HIV-2). Various genera within the Flaviviridae family include *Flavivirus, Pestivirus, Hepacivirus* and Hepatitis G Virus. Members of the *Flavivirus* genus include Dengue fever virus, yellow fever virus, West Nile encephalitis virus and Japanese encephalitis virus. Members of the *Pestivirus* genus include bovine viral diarrhoea virus (BVDV), classical swine fever virus and border disease virus 2 (BDV-2). Members of the *Hepacivirus* genus include hepatitis C virus (HCV). Members of the Hepatitis G Virus genus include hepatitis G virus. Various genera within the Picornaviridae family include *Aphthovirus, Avihepatovirus, Cardiovirus, Enterovirus, Erbovirus, Hepatovirus, Kobuvirus, Parechovirus, Sapelovirus, Senecavirus, Teschovirus* and *Tremovirus*. Members of the *Enterovirus* genus include poliovirus, coxsackie A virus, coxsackie B virus and rhinovirus.

Organ transplant rejection includes the rejection of transplanted or grafted organs or cells (both allografts and xenografts), including graft-versus-host reaction disease. The term "organ" as used herein means all organs or parts of organs in mammals, particularly humans, including kidney, lung, bone marrow, hair, cornea, eye (vitreous), heart, heart valve, liver, pancreas, blood vessel, skin, muscle, bone, intestine and stomach. The term "rejection" as used herein means all reactions of the recipient body or the transplanted organ which ultimately lead to cell or tissue death in the transplanted organ, or adversely affect the functional ability and viability of the transplanted organ or the recipient. In particular, this means acute and chronic rejection reactions.

Cell transplant rejection includes the rejection of cell transplants and xenotransplantation. The major hurdle for xenotransplantation is that even before the T lymphocytes (responsible for the rejection of allografts) are activated, the innate immune system (especially T-independent B lymphocytes and macrophages) is activated. This provokes two types of severe and early acute rejection, referred to as hyperacute rejection and vascular rejection respectively. Conventional immunosuppressant drugs, including cyclosporine A, are ineffective in xenotransplantation. The compounds in accordance with the present invention are not liable to this drawback. The ability of the compounds of this invention to suppress T-independent xeno-antibody production as well as macrophage activation may be demonstrated by their ability to prevent xenograft rejection in athymic, T-deficient mice receiving xenogenic hamster-heart grafts.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (IA) or (IB) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (IA) or (IB) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (IA) or (IB) above may be prepared by a process which comprises reacting a compound of formula Q-H with a compound of formula (IIIA) or (IIIB):

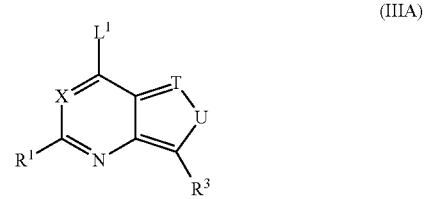

(IIIA)

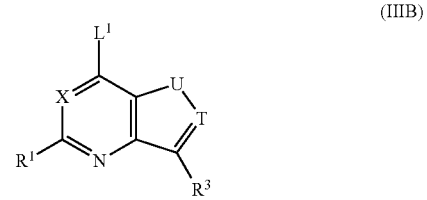

(IIIB)

wherein X, T, U, Q, $R^1$ and $R^3$ are as defined above, and $L^1$ represents a suitable leaving group.

The leaving group $L^1$ is typically a halogen atom, e.g. chloro.

The reaction will generally be carried out in the presence of a base, typically an organic amine such as triethylamine or N,N-diisopropylethylamine. The reaction is conveniently effected at ambient or elevated temperature in a suitable solvent, e.g. a lower alkanol such as ethanol or n-butanol, a cyclic ether solvent such as tetrahydrofuran, 2-methyltetrahydrofuran or 1,4-dioxane, or a dipolar aprotic solvent such as N,N-dimethylformamide.

Alternatively, the leaving group $L^1$ may be hydroxy (—OH), in which case the reaction may be accomplished at a suitable temperature (ambient or elevated) in a solvent such as acetonitrile or N,N-dimethylformamide, ideally in the presence of a coupling agent such as benzotriazol-1-yloxytris(dimethylamino)phosphonium hexafluorophosphate (BOP) or (benzotriazol-1-yloxy)tripyrrolidinophosphonium hexafluorophosphate (PyBOP), and a base, e.g. an organic base such as 1,8-diazabicyclo[5.4.0]undec-7-ene (DBU).

In another procedure, the compounds of formula (IA) or (IB) above wherein Y represents —C(O)—, —S(O)$_2$— or —C(O)O— may be prepared by a process which comprises reacting a compound of formula $L^2$-C(O)—Z, $L^2$-S(O)$_2$—Z or $L^2$-C(O)O—Z respectively with a compound of formula (IVA-1), (IVA-2), (IVA-3), (IVA-4), (IVA-5), (IVB-1), (IVB-2), (IVB-3), (IVB-4) or (IVB-5):

(IVA-1)

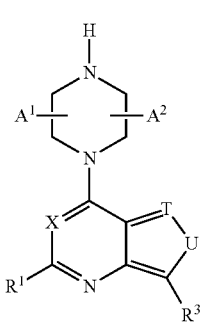

(IVA-2)

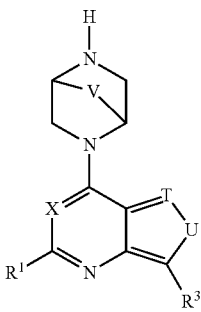

(IVA-3)

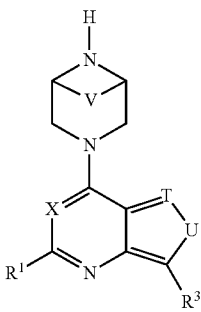

-continued (IVA-4)

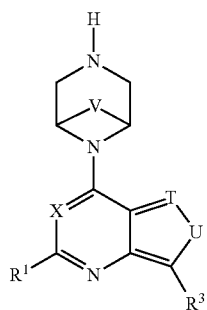

(IVA-5)

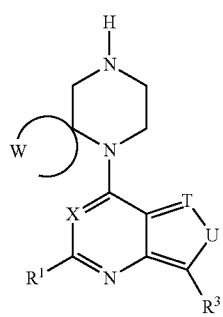

(IVB-1)

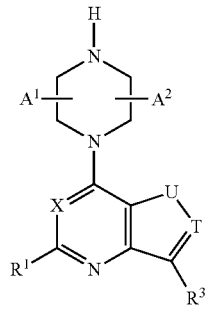

(IVB-2)

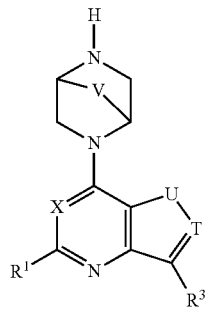

(IVB-3)

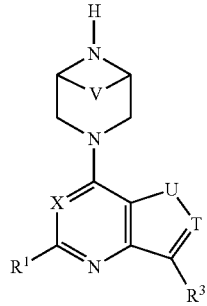

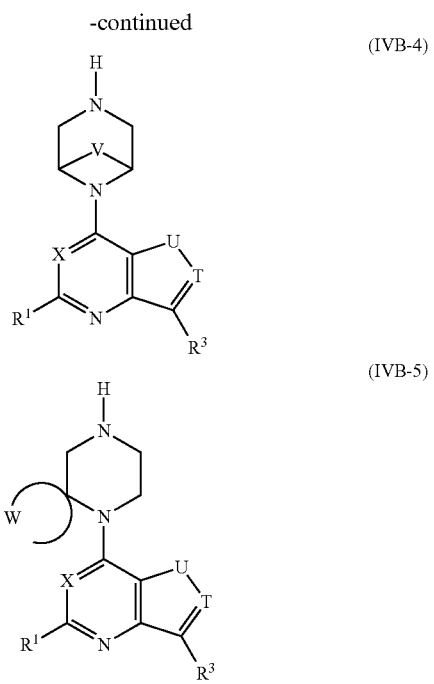

wherein X, T, U, V, W, Z, A$^1$, A$^2$, R$^1$ and R$^3$ are as defined above, and L$^2$ represents a suitable leaving group.

The leaving group L$^2$ is typically a halogen atom, e.g. chloro.

The reaction is conveniently effected at ambient temperature in a suitable solvent, e.g. an ethereal solvent such as 1,4-dioxane, or a chlorinated solvent such as dichloromethane, typically in the presence of a base. A suitable base for use in the reaction may be an organic base such as N,N-diisopropylethylamine, or an inorganic base such as potassium carbonate.

Alternatively, the leaving group L$^2$ may be 2-methyl-3-(trifluoromethylsulfonyl)-1H-imidazol-3-ium-1-yl, in which case the reaction may conveniently be effected at ambient temperature in an organic solvent such as acetonitrile.

In a variant procedure, the compounds of formula (IA) or (IB) above wherein Y represents —C(O)— may be prepared by a process which comprises reacting a compound of formula (IVA-1), (IVA-2), (IVA-3), (IVA-4), (IVA-5), (IVB-1), (IVB-2), (IVB-3), (IVB-4) or (IVB-5) as defined above with a compound of formula Z—CO$_2$H. Similarly, the compounds of formula (IA) or (IB) above wherein Y represents —C(O)C(O)— may be prepared by a process which comprises reacting a compound of formula (IVA-1), (IVA-2), (IVA-3), (IVA-4), (IVA-5), (IVB-1), (IVB-2), (IVB-3), (IVB-4) or (IVB-5) as defined above with a compound of formula Z—C(O)CO$_2$H.

The reaction is conveniently effected at ambient temperature in a suitable solvent, e.g. a dipolar aprotic solvent such as N,N-dimethylformamide, typically in the presence of a coupling reagent and a base. A suitable coupling reagent for use in the reaction may be O-(7-azabenzotriazol-1-yl)-N,N,N',N'-tetramethyluronium hexafluorophosphate (HATU). A suitable base for use in the reaction may be an organic base such as N,N-diisopropylethylamine.

In another procedure, the compounds of formula (IA) or (IB) above wherein Y represents —C(O)NH— may be prepared by a process which comprises reacting a compound of formula (IVA-1), (IVA-2), (IVA-3), (IVA-4), (IVA-5), (IVB-1), (IVB-2), (IVB-3), (IVB-4) or (IVB-5) as defined above with an isocyanate derivative of formula Z—N=C=O, wherein Z is as defined above.

The reaction is conveniently effected at a suitable temperature, e.g. ambient temperature or a temperature in the region of 0° C., in a suitable solvent or mixture of solvents. Such solvent or solvents may typically be selected as appropriate from an ethereal solvent such as 1,4-dioxane or tetrahydrofuran, a chlorinated solvent such as dichloromethane, a nitrile-containing solvent such as acetonitrile, and a dipolar aprotic solvent such as N,N-dimethylformamide. The reaction may optionally be performed in the presence of a base, e.g. an organic base such as diisopropylamine, N,N-diisopropylethylamine or triethylamine.

Alternatively, the compounds of formula (IA) or (IB) above wherein Y represents —C(O)NH— may be prepared by a process which comprises reacting a compound of formula (IVA-1), (IVA-2), (IVA-3), (IVA-4), (IVA-5), (IVB-1), (IVB-2), (IVB-3), (IVB-4) or (IVB-5) as defined above with a compound of formula Z—NH$_2$, wherein Z is as defined above, in the presence of triphosgene or 1,1'-carbonyldiimidazole.

The reaction is conveniently effected at ambient temperature in a suitable solvent, e.g. a chlorinated solvent such as dichloromethane, or a dipolar aprotic solvent such as N,N-dimethylformamide, typically in the presence of a base, e.g. an organic base such as N,N-diisopropylethylamine.

Alternatively, the compounds of formula (IA) or (IB) above wherein Y represents —C(O)NH— may be prepared by a two-step process which comprises: (i) reacting a compound of formula Z—NH$_2$, wherein Z is as defined above, with phenyl chloroformate; and (ii) reacting the material thereby obtained with a compound of formula (IVA-1), (IVA-2), (IVA-3), (IVA-4), (IVA-5), (IVB-1), (IVB-2), (IVB-3), (IVB-4) or (IVB-5) as defined above.

Step (i) of the above process is conveniently effected at a suitable temperature, e.g. ambient temperature or a temperature in the region of 0° C., in a suitable solvent, e.g. a cyclic ether solvent such as tetrahydrofuran or a chlorinated solvent such as dichloromethane, typically in the presence of a base, e.g. an organic base such as pyridine or triethylamine. Step (ii) is conveniently effected at ambient or elevated temperature in a suitable solvent, e.g. a sulfoxide solvent such as dimethyl sulfoxide, or a nitrile-containing solvent such as acetonitrile, or a C$_{1-4}$ alkanol such as ethanol, or a chlorinated solvent such as dichloromethane, typically in the presence of a base, e.g. an organic base such as N,N-diisopropylethylamine.

In a further procedure, the compounds of formula (IA) or (IB) above wherein Y represents —S(O)$_2$NH— may be prepared by a two-step process which comprises: (i) reacting a compound of formula (IVA-1), (IVA-2), (IVA-3), (IVA-4), (IVA-5), (IVB-1), (IVB-2), (IVB-3), (IVB-4) or (IVB-5) as defined above with methyl trifluoromethanesulfonate; and (ii) reacting the material thereby obtained with a compound of formula Z—NH$_2$, wherein Z is as defined above.

Step (i) of the above process is conveniently effected at a temperature in the region of 0° C. in a suitable solvent, typically a chlorinated solvent such as dichloromethane. Step (ii) is conveniently effected at an elevated temperature in a suitable solvent, e.g. a nitrile-containing solvent such as acetonitrile.

In a further procedure, the compounds of formula (IA) or (IB) above wherein Y represents a covalent bond, and Z represents optionally substituted C$_{1-6}$ alkyl, optionally substituted C$_{3-7}$ cycloalkyl(C$_{1-6}$)alkyl, optionally substituted C$_{3-7}$ heterocycloalkyl(C$_{1-6}$)-alkyl, optionally substituted aryl(C$_{1-6}$)alkyl or optionally substituted heteroaryl(C$_{1-6}$) alkyl, may be prepared by a process which comprises reacting a compound of formula (IVA-1), (IVA-2), (IVA-3), (IVA-4), (IVA-5), (IVB-1), (IVB-2), (IVB-3), (IVB-4) or (IVB-5) as defined above with a compound of formula Z$^1$-L$^3$ wherein Z$^1$ represents C$_{1-6}$ alkyl, C$_{3-7}$ cycloalkyl(C$_{1-6}$)alkyl, aryl(C$_{1-6}$)alkyl, C$_{3-7}$ heterocycloalkyl(C$_{1-6}$)alkyl or heteroaryl(C$_{1-6}$)-alkyl, any of which groups may be optionally substituted by one or more substituents, and L$^3$ represents a suitable leaving group.

The leaving group L$^3$ is typically a halogen atom.

The reaction is conveniently effected at ambient temperature in a suitable solvent, e.g. a dipolar aprotic solvent such as N,N-dimethylformamide, or a chlorinated solvent such as dichloromethane, typically in the presence of a base. A suitable base for use in the reaction may be an organic base such as triethylamine, or an inorganic base such as caesium carbonate.

In a variant procedure, the compounds of formula (IA) or (IB) above wherein Y represents a covalent bond, and Z represents optionally substituted C$_{1-6}$ alkyl, optionally substituted C$_{3-7}$ cycloalkyl(C$_{1-6}$)alkyl, optionally substituted C$_{3-7}$ heterocycloalkyl(C$_{1-6}$)-alkyl, optionally substituted aryl(C$_{1-6}$)alkyl or optionally substituted heteroaryl(C$_{1-6}$) alkyl, may be prepared by a two-step process which comprises: (i) reacting a compound of formula (IVA-1), (IVA-2), (IVA-3), (IVA-4), (IVA-5), (IVB-1), (IVB-2), (IVB-3), (IVB-4) or (IVB-5) as defined above with a compound of formula Z$^2$—CHO, wherein Z$^2$—CH$_2$— corresponds to a group of formula Z$^1$— as defined above; and (ii) reacting the material thereby obtained with a reducing agent.

Steps (i) and (ii) of the above process are conveniently effected at ambient temperature in a suitable solvent, e.g. a C$_{1-4}$ alkanol such as methanol. Step (i) is typically performed in the presence of a base, e.g. an organic base such as triethylamine. The reducing agent for use in step (ii) may suitably be an alkali metal borohydride such as sodium borohydride.

The compounds of formula (IA) or (IB) above wherein Y represents a linker group of formula (Ya) as defined above may be prepared by a process which comprises reacting a compound of formula (IVA-1), (IVA-2), (IVA-3), (IVA-4), (IVA-5), (IVB-1), (IVB-2), (IVB-3), (IVB-4) or (IVB-5) as defined above with a compound of formula (V):

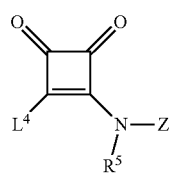

(V)

wherein Z and R$^5$ are as defined above, and L$^4$ represents a suitable leaving group.

The leaving group L$^4$ is typically a C$_{1-4}$ alkoxy group, e.g. ethoxy.

The reaction is conveniently effected at ambient temperature in a suitable solvent, e.g. a lower alkanol such as ethanol, typically in the presence of a base, e.g. an organic base such as triethylamine.

The intermediates of formula (IVA-1), (IVA-2), (IVA-3), (IVA-4), (IVA-5), (IVB-1), (IVB-2), (IVB-3), (IVB-4) or (IVB-5) above may be prepared by reacting a compound of formula (IIIA) or (IIIB) as defined above with a compound of formula (VIA), (VIB), (VIC), (VID) or (VIE):

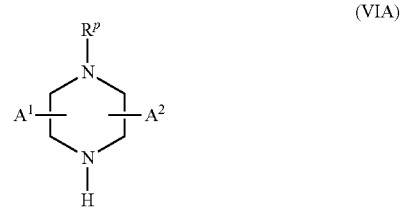

(VIA)

(VIB)

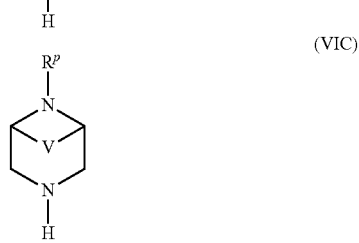

(VIC)

(VID)

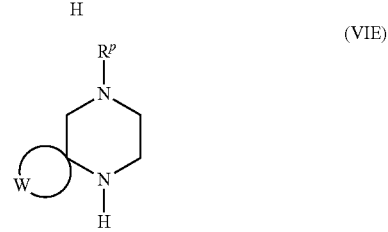

(VIE)

wherein V, W, A$^1$ and A$^2$ are as defined above, and R$^p$ represents hydrogen or an N-protecting group; followed, as necessary, by removal of the N-protecting group R$^p$.

In one embodiment, the N-protecting group R$^p$ is typically tert-butoxycarbonyl (BOC).

In another embodiment, the N-protecting group R$^p$ is typically benzyl.

The reaction between compound (IIIA) or (IIIB) and compound (VIA), (VIB), (VIC), (VID) or (VIE) is conveniently accomplished under conditions analogous to those described above for the reaction between the compound of formula Q-H and compound (IIIA) or (IIIB).

Where the N-protecting group R$^p$ is BOC, subsequent removal of the BOC group may typically be accomplished by treatment with an acid, e.g. a mineral acid such as hydrochloric acid or sulphuric acid, or an organic acid such as trifluoroacetic acid. Alternatively, the BOC group may be removed by treatment with trimethylsilyl trifluoromethanesulfonate and 2,6-lutidine, typically at ambient temperature in a suitable solvent, e.g. a chlorinated solvent such as dichloromethane. Alternatively, the BOC group may be removed by treatment with trimethylsilyl iodide, typically at ambient temperature in a suitable solvent, e.g. a chlorinated solvent such as chloroform.

Where the N-protecting group $R^p$ is benzyl, subsequent removal of the benzyl group may typically be accomplished by catalytic hydrogenation. Suitably, transfer hydrogenation conditions will be employed. A suitable hydrogenation catalyst of use in this procedure may be a transition metal catalyst such as palladium on carbon. The reaction will conveniently be performed at an elevated temperature in the presence of a hydrogen donor such as ammonium formate.

The intermediates of formula (IIIA) or (IIIB) above wherein $L^1$ is chloro may be prepared by treating a compound of formula (VIIA) or (VIIB):

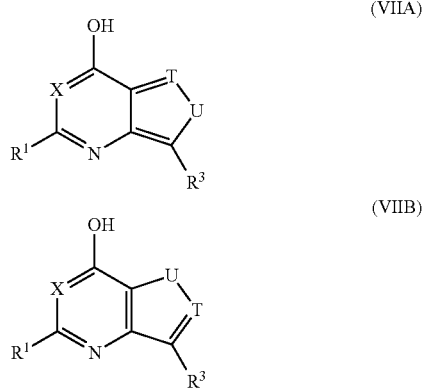

wherein X, T, U, $R^1$ and $R^3$ are as defined above; with a chlorinating agent.

A suitable chlorinating agent for use in the above procedure is phosphorus oxychloride.

The reaction is conveniently effected by mixing the reagents at an elevated temperature, typically in the presence of a base, e.g. an organic amine such as N,N-diisopropylethylamine or N,N-dimethylaniline.

As will be appreciated, the intermediates of formula (IVA-1), (IVA-2), (IVA-3), (IVA-4), (IVA-5), (IVB-1), (IVB-2), (IVB-3), (IVB-4) and (IVB-5) correspond to compounds in accordance with the present invention wherein Y represents a covalent bond and Z is hydrogen. Similarly, the intermediates of formula (VIA), (VIB), (VIC), (VID) or (VIIE) wherein $R^p$ is hydrogen correspond to intermediates of formula Q-H wherein Y represents a covalent bond and Z is hydrogen. Likewise, the intermediates of formula (VIA), (VIB), (VIC), (VID) or (VIE) wherein $R^p$ is BOC correspond to intermediates of formula Q-H wherein Y represents —C(O)O— and Z is tert-butyl. Furthermore, the intermediates of formula (VIA), (VIB), (VIC), (VID) or (VIE) wherein $R^p$ is benzyl correspond to intermediates of formula Q-H wherein Y represents a covalent bond and Z is benzyl. The intermediates of formula (VIIA) and (VIIB) correspond to intermediates of formula (IIIA) or (IIIB) wherein $L^1$ is hydroxy.

Where they are not commercially available, the starting materials of formula (V), (VIA), (VIB), (VIC), (VID), (VIE), (VIIA) and (VIIB) may be prepared by methods analogous to those described in the accompanying Examples, or by standard methods well known from the art.

It will be understood that any compound of formula (IA) or (IB) initially obtained from any of the above processes may, where appropriate, subsequently be elaborated into a further compound of formula (IA) or (IB) by techniques known from the art. By way of example, a compound comprising a N—BOC moiety may be converted into the corresponding compound comprising a N—H moiety by treatment with an acid, e.g. a mineral acid such as hydrochloric acid, or an organic acid such as trifluoroacetic acid.

A compound wherein $R^1$ represents halogen, e.g. chloro, may be converted into the corresponding compound wherein $R^1$ represents amino (—NH$_2$) in a two-step procedure which comprises: (i) treatment with benzylamine or 4-methoxybenzylamine; and (ii) removal of the benzyl or 4-methoxybenzyl moiety from the material thereby obtained by catalytic hydrogenation or by treatment with an acid, e.g. a mineral acid such as sulfuric acid, or an organic acid such as trifluoroacetic acid.

A compound wherein $R^1$ represents —$SR^a$ may be converted into the corresponding compound wherein $R^1$ represents —$SO_2R^a$ by treatment with an oxidising agent, typically 3-chloroperoxybenzoic acid (MCPBA).

A compound wherein $R^1$ represents —$SO_2R^a$, e.g. methylsulfonyl, may be converted into the corresponding compound wherein $R^1$ represents —$OR^a$ by treatment with a sodium salt of formula Na$OR^a$. Similarly, a compound wherein $R^1$ represents —$SO_2R^a$, e.g. methylsulfonyl, may be converted into the corresponding compound wherein $R^1$ represents cyano by treatment with a cyanide salt, e.g. an alkali metal cyanide salt such as sodium cyanide. Likewise, a compound wherein $R^1$ represents —$SO_2R^a$, e.g. methylsulfonyl, may be converted into the corresponding compound wherein $R^1$ represents —$NR^bR^c$ by treatment with an amine of formula H—$NR^bR^c$. By analogy, a compound wherein $R^1$ represents —$SO_2R^a$, e.g. methylsulfonyl, may be converted into the corresponding compound wherein $R^1$ represents —$NH_2$ by treatment with ammonium hydroxide.

A compound wherein $R^2$ represents —$CO_2R^d$, in which $R^d$ is other than hydrogen, may be converted into the corresponding compound wherein $R^2$ represents carboxy (—$CO_2H$) by treatment with a base, typically an alkali metal hydroxide such as sodium hydroxide.

A compound wherein $R^2$ represents carboxy (—$CO_2H$) may be converted into the corresponding compound wherein $R^2$ represents —$CONR^bR^c$ or —$CON(OR^a)R^b$ by treatment with the appropriate reagent of formula H—$NR^bR^c$ or H—N(O$R^a$)$R^b$ respectively. The reaction may typically be performed in the presence of a coupling agent such as 1-(3-dimethylaminopropyl)-3-ethylcarbodiimide hydrochloride (EDC) and an additive such as 1-hydroxybenzotriazole hydrate (HOBT), optionally in the presence of a base, e.g. an organic base such as N,N-diisopropylethylamine. Alternatively, the reaction may be performed in the presence of a coupling agent such as O-(benzotriazol-1-yl)-N,N,N',N'-tetramethyluronium tetrafluoroborate (TBTU) and a base, e.g. an organic base such as N,N-diisopropylethylamine.

A compound wherein $R^2$ represents carboxy (—$CO_2H$) may be converted into the corresponding compound wherein $R^2$ represents —$CONH_2$ by treatment with ammonium chloride, typically in the presence of a coupling agent such as EDC and an additive such as HOBT, suitably in the presence of a base, e.g. an organic base such as diisopropylamine or N,N-diisopropylethylamine. A compound wherein $R^2$ represents —$CONH_2$ may be converted into the corresponding compound wherein $R^2$ represents cyano (—CN) by treatment with phosphorus oxychloride. Alternatively, a compound wherein $R^2$ represents —$CONH_2$ may be converted into the corresponding compound wherein $R^2$ represents cyano in a two-step procedure which comprises: (i) treatment with cyanuric chloride; and (ii) treatment of the material thereby obtained with water.

A compound wherein $R^2$ represents carboxy (—$CO_2H$) may be converted into the corresponding compound wherein $R^2$ represents hydrogen by heating in the presence of a base, e.g. an organic amine such as triethylamine.

A compound wherein $R^2$ represents carboxy (—$CO_2H$) may be converted into the corresponding compound wherein $R^2$ represents hydroxymethyl (—$CH_2OH$) in a two-step procedure which comprises: (i) treatment with ethyl chloroformate and triethylamine; and (ii) treatment of the material thereby obtained with a reducing agent, typically an alkali metal borohydride such as sodium borohydride.

A compound wherein $R^2$ represents carboxy (—$CO_2H$) may be converted into the corresponding compound wherein $R^2$ represents hydroxy in a two-step procedure which comprises: (i) treatment with diphenyl phosphoryl azide; and (ii) treatment of the material thereby obtained with water.

A compound wherein $R^2$ represents carboxy (—$CO_2H$) may be converted into the corresponding compound wherein $R^2$ represents —$NHCO_2R^d$, wherein $R^d$ is other than hydrogen, in a two-step procedure which comprises: (i) treatment with diphenyl phosphoryl azide; and (ii) treatment of the material thereby obtained with the appropriate reagent of formula $R^d$—OH.

A compound wherein $R^2$ represents carboxy (—$CO_2H$) may be converted into the corresponding compound wherein $R^2$ represents a 3-substituted 1,2,4-oxadiazol-5-yl moiety in a two-step procedure which comprises: (i) treatment with an appropriately-substituted N'-hydroxyamidine derivative, typically in the presence of a coupling agent such as O-(7-azabenzotriazol-1-yl)-N,N,N',N'-tetramethyluronium hexafluorophosphate (HATU), suitably in the presence of a base, e.g. an organic base such as N,N-diisopropylethylamine; and (ii) treatment of the material thereby obtained with a strong base, suitably a strong inorganic base, e.g. an alkali metal tert-butoxide such as potassium tert-butoxide.

A compound wherein $R^2$ represents 4,5-dihydrooxazol-2-yl may be prepared from the corresponding compound wherein $R^2$ represents —$CONR^bR^c$, in which $R^b$ represents —$CH_2CH_2OH$ and $R^c$ represents hydrogen, by heating with a condensing agent such as N,N'-diisopropylcarbodiimide, typically in the presence of copper(II) trifluoromethanesulfonate.

A compound wherein $R^4$ represents hydrogen may be converted into the corresponding compound wherein $R^4$ represents $C_{1-6}$ alkyl, e.g. methyl, by treatment with a $C_{1-6}$ alkyl halide, e.g. iodomethane, usually in the presence of a base, suitably an inorganic base, e.g. potassium carbonate.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (IA) or (IB) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (IA) or (IB), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (IA) or (IB) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human PI4KIIIβ.

PI4KIIIβ Enzyme Inhibition Assay

Procedure A

Compounds were assayed utilizing reagents from Invitrogen and Promega. Compounds were screened in 1% DMSO (final) as 3-fold serial dilutions from a starting concentration of 20 μM. The 2.5×PI4Kβ reagent, the 2.5×PI Lipid Kinase Substrate/ATP mixture and the 5× compounds were prepared in 20 mM Tris pH 7.5, 0.5 mM EGTA, 2 mM DTT, 5 mM $MgCl_2$, 0.4% Triton. The final 25 μL Kinase Reaction consisted of: 4 nM PI4Kβ, 100 μM PI Lipid Kinase Substrate (both Invitrogen), and compound. The final ATP concentration in the assay was 10 μM. The detection reagents consisted of ADP-Glo™ Reagent and ADP-Glo™ Detect Reagent (Promega).

Briefly, compound was added to PI4Kβ followed by addition of ATP/PI Lipid Kinase Substrate mixture. The reaction mixture was incubated for 60 minutes at room temperature. The ADP-Glo™ Reagent was added and the plate was incubated for 40 minutes at room temperature, followed by addition of ADP-Glo™ Detect Reagent. The plate was incubated for a further 120 minutes and read on a Luminescence plate reader. The data was fitted with XLfit from IDBS using model number 205.

Procedure B

Compounds were assayed using a PI4Kbeta Adapta assay. Compounds were screened in 1% DMSO (final) as 3-fold serial dilutions from a starting concentration of 10 μM. The 2×PI4 KB (PI4K beta)/PI Lipid Kinase Substrate mixture was prepared in 50 mM HEPES pH 7.5, 0.1% CHAPS, 1 mM EGTA, 4 mM $MgCl_2$. The final 10 μL Kinase Reaction consisted of 7.5-60 ng PI4Kβ, and 100 μM PI Lipid Kinase Substrate in 32.5 mM HEPES pH 7.5, 0.05% CHAPS, 0.5 mM EGTA, 2 mM $MgCl_2$. The final ATP concentration in the assay was 10 μM. The detection mix consisted of EDTA (30 mM), Eu-anti-ADP antibody (6 nM) and ADP tracer. The detection mix contained the EC60 concentration of tracer for 5-150 μM ATP.

Briefly, ATP was added to compound, followed by addition of a PI4Kβ/PI Lipid Kinase Substrate mixture. The plate was shaken for 30 seconds to mix, then briefly centrifuged. The reaction mixture was incubated for 60 minutes at room temperature. The detection mix was added, then the plate was shaken and centrifuged. The plate was incubated for 60 minutes at room temperature and read on a fluorescence plate reader. The data was fitted with XLfit from IDBS using model number 205.

When tested in the above assay (Procedure A or Procedure B), the compounds of the accompanying Examples were all found to possess $IC_{50}$ values for inhibition of the activity of human PI4KIIIβ of 50 μM or better.

Certain compounds in accordance with this invention are potent inhibitors when measured in the MLR test described below.

The Mixed Lymphocyte Reaction (MLR) Test

Human peripheral blood mononuclear cells (PBMCs) were isolated from buffy coats, obtained from healthy blood donors by Ficoll (Lymphoprep, Axis-Shield PoC AS, Oslo, Norway) density-gradient centrifugation. The cells at the Ficoll-plasma interface were washed three times and used as "Responder" cells. RPMI 1788 (ATCC, N° CCL-156) cells were treated with mitomycin C (Kyowa, Nycomed, Brussels, Belgium) and used as "Stimulator" cells. Responder cells (0.12×106), Stimulator cells (0.045×106) and compounds (in different concentrations) were cocultured for 6 days in RPMI 1640 medium (BioWhittaker, Lonza, Belgium) supplemented with 10% fetal calf serum, 100 U/ml Geneticin (Gibco, LifeTechnologies, UK). Cells were cultured in triplicate in flat-bottomed 96-well microtiter tissue culture plates (TTP, Switzerland). After 5 days, cells were pulsed with 1 μCi of methyl-$^3$H thymidine (MP Biomedicals, USA), harvested 18 h later on glass filter paper and counted. Proliferation values were expressed as counts per minute (cpm), and converted to % inhibition with respect to a blank MLR test (identical but without added compound). The $IC_{50}$ was determined from a graph with at least four points, each derived from the mean of 2 experiments. The $IC_{50}$ value represents the lowest concentration of test compound (expressed in μM) that resulted in a 50% inhibition of the MLR.

Certain compounds of the accompanying Examples were found to generate $IC_{50}$ values in the MLR test of 10 μM or better.

EXAMPLES

Abbreviations

THF: tetrahydrofuran
DMF: N,N-dimethylformamide
DCM: dichloromethane
EtOH: ethanol EtOAc: ethyl acetate
MeCN: acetonitrile
TFA: trifluoroacetic acid
NMP: 1-methyl-2-pyrrolidinone
DBU: 1,8-diazabicyclo[5.4.0]undec-7-ene DIC: N,N'-diisopropylcarbodiimide
MeOH: methanol
DMSO: dimethyl sulfoxide
DIPEA: N,N-diisopropylethylamine
MCPBA: 3-chloroperoxybenzoic acid
Et$_2$O: diethyl ether BOP: (Benzotriazol-1-yloxy)tris(dimethylamino)phosphonium hexafluorophosphate
PyBOP: (Benzotriazol-1-yloxy)tripyrrolidinophosphonium hexafluorophosphate
TBTU: O-(Benzotriazol-1-yl)-N,N,N',N'-tetramethyluronium tetrafluoroborate
h: hour
MS: Mass Spectrometry
LCMS: Liquid Chromatography Mass Spectrometry
ES+: Electrospray Positive Ionisation
HPLC: High Performance Liquid Chromatography
TLC: thin layer chromatography
r.t.: room temperature
M: mass
RT: retention time
Analytical Methods
Method 1
High pH (approximately pH 9.5)
Column: Waters XBridge, C18, 2.1×20 mm, 2.5 μm
Solvent A: 10 mM ammonium formate in water+0.1% ammonia solution
Solvent B: acetonitrile+5% solvent A+0.1% ammonia solution
Gradient Program:

| Time | A % | B % |
| --- | --- | --- |
| 0.00 | 95.0 | 5.0 |
| 1.50 | 5.0 | 95.0 |
| 2.50 | 5.0 | 95.0 |
| 3.00 | 95.0 | 5.0 |

Method 2
High pH (approximately pH 9.5)
Column: Waters XBridge, C18, 2.1×20 mm, 2.5 μm
Solvent A: 10 mM ammonium formate in water+0.1% ammonia solution
Solvent B: acetonitrile+5% solvent A+0.1% ammonia solution
Gradient Program:

| Time | A % | B % |
| --- | --- | --- |
| 0.00 | 95.0 | 5.0 |
| 4.00 | 5.0 | 95.0 |
| 5.00 | 5.0 | 95.0 |
| 5.10 | 95.0 | 5.0 |

5.10 95.0 5.0

Intermediate 1

Methyl 2-amino-4-hydroxythieno[3,4-d]pyrimidine-5-carboxylate

A mixture of dimethyl 4-aminothiophene-2,3-dicarboxylate (1.08 g, 5 mmol), chloroformamidine hydrochloride (1.44 g, 12.5 mmol) and dimethyl sulfone (2.35 g, 25 mmol) was finely ground with a pestle and mortar, and the mixture was heated at 130° C. for 40 minutes, then cooled to r.t. Water was poured into the reaction mixture, and concentrated ammonia solution was added to basify the reaction solution (ice bath). The precipitate was collected, washed with water and dried in vacuo to provide the title compound (1.1 g, 97%) as a yellow solid. $^{13}$C NMR (75 MHz, DMSO-d$_6$) δ 161.1, 156.8, 151.3, 151.2, 131.8, 123.1, 113.5, 52.6. MS m/z (%) 226 [M+H]$^+$.

Intermediate 2

Methyl 2-amino-4-(piperazin-1-yl)thieno[3,4-d]pyrimidine-5-carboxylate

To a suspension of Intermediate 1 (6.78 g, 30.11 mmol), piperazine (7.7 g, 90.23 mmol) and BOP (13.3 g, 30.11 mmol) in DMF (100 mL) was added DBU (6.7 mL, 45.16 mmol). The reaction mixture was stirred at r.t. for 16 h. The solvent was evaporated in vacuo, then the residue was purified by silica gel chromatography (DCM:MeOH:NH$_3$-MeOH 100:10:1), to provide the title compound (3.6 g, 41%) as a yellow solid. δ$_H$ (300 MHz, DMSO-d$_6$) 7.42 (s, 1H), 6.16 (s, 2H), 3.84 (s, 3H), 3.52 (s, 4H), 2.76 (s, 4H). MS m/z (%) 294 [M+H]$^+$.

Intermediate 3

Methyl 2-amino-4-[4-(tert-butoxycarbonyl)piperazin-1-yl]thieno[3,4-d]pyrimidine-5-carboxylate To a solution of Intermediate 2 (0.82 g, 2.79 mmol) in DMF (10 mL) were added di-tert-butyl dicarbonate (0.73 g, 3.35 mmol) and triethylamine (0.47 mL, 3.35 mmol). The reaction mixture was stirred at room temperature for 5 h, then partitioned between DCM and water. The layers were separated, and the aqueous layer was extracted twice with DCM. The combined organic phases were dried with anhydrous MgSO$_4$. The solvent was evaporated in vacuo, and the residue was precipitated in a mixture of EtOAc and hexane, to provide the title compound (0.96 g, 87%) as a yellow solid. MS m/z (%) 394 [M+H]$^+$.

Intermediate 4

2-Amino-4-[4-(tert-butoxycarbonyl)piperazin-1-yl]thieno[3,4-d]pyrimidine-5-carboxylic acid To a suspension of Intermediate 3 (1.1 g, 2.79 mmol) in a mixture of MeOH and water (10:1, 11 mL) was added 40% aqueous NaOH solution (0.95 mL, 13.97 mmol). The reaction mixture was heated at reflux for 3 h, then concentrated and dissolved in water (5 mL). Concentrated HCl was added dropwise to acidify the solution to pH 4-5 (ice bath). The resulting precipitate was collected, washed with water and dried in vacuo to provide the title compound (0.73 g, 68%) as a yellow solid. MS m/z (%) 380 [M+H]$^+$.

Intermediate 5 tert-Butyl 4-(2-aminothieno[3,4-d]pyrimidin-4-yl)piperazine-1-carboxylate

A solution of Intermediate 4 (76 mg, 0.2 mmol) and triethylamine (84 µL, 0.6 mmol) in DMF (6 mL) was heated at 100° C. for 2 h. The reaction mixture was concentrated to dryness giving the title compound (66 mg, 98%) as a yellowish solid. MS m/z (%) 336 [M+H]$^+$.

Intermediate 6

4-(Piperazin-1-yl)thieno[3,4-d]pyrimidin-2-amine

Intermediate 5 (66 mg, 0.2 mmol) was dissolved in a mixture of 4M HCl in 1,4-dioxane (1 mL) and MeOH (1 mL). The reaction mixture was stirred at room temperature for 3 h, then evaporated to dryness and co-evaporated twice with ammonia in MeOH, to provide the title compound (47 mg, 100%) as a yellow solid. MS m/z (%) 236 [M+H]$^+$.

Intermediate 7

2-Aminothieno[3,4-d]pyrimidin-4-ol

A mixture of methyl 4-aminothiophene-3-carboxylate (1.0 g, 6.4 mmol), chloroformamidine hydrochloride (1.83 g 15.9 mmol) and dimethyl sulfone (2.99 g, 31.8 mmol) was finely ground with a pestle and mortar, and the mixture was heated at 130° C. for 40 minutes. Water was poured into the reaction mixture, and concentrated ammonia solution was added to basify the reaction solution (ice bath). The precipitate was collected, washed with water and dried in vacuo, to provide the title compound (0.99 g, 92%) as a yellow solid. $^{13}$C NMR (75 MHz, DMSO-d6) δ 159.7, 151.4, 148.8, 127.4, 123.7, 108.4. MS m/z (%) 168 [M+H]$^+$.

Intermediate 8

2-Amino-4-{4-[(4-methoxyphenyl)carbamoyl]piperazin-1-yl}thieno[3,4-d]pyrimidine-5-carboxylic acid Intermediate 4 (76 mg, 0.2 mmol) was dissolved in a mixture of 4M HCl in 1,4-dioxane (1 mL) and MeOH (1.25M, 1 mL). The reaction mixture was stirred at room temperature for 1.5 h, then evaporated to dryness, and twice co-evaporated with ammonia in MeOH. The resulting crude material was suspended in DMF (10 mL) and treated with 4-methoxyphenyl isocyanate (26 µL, 0.2 mmol). The reaction mixture turned clear, and was stirred at room temperature for 2 h. The reaction mixture was concentrated, and the residue was precipitated in a small amount of water. The precipitate was collected, and washed with water and EtOH, then dried in vacuo, to yield the title compound (73 mg, 85% overall) as a yellow solid. δ$_H$ (300 MHz, DMSO-d$_6$) 8.49 (s, 1H), 8.09 (s, 2H), 7.29 (d, 2H, J 9.0 Hz), 7.07 (s, 1H), 6.79 (d, 2H, J 9.0 Hz), 3.96 (m, 4H), 3.69 (s, 3H), 3.59 (m, 4H). MS m/z (%) 429 [M+H]$^+$.

Intermediate 9

2-Amino-N-(2-hydroxyethyl)-4-{4-[(4-methoxyphenyl)carbamoyl]piperazin-1-yl}thieno-[3,4-d]pyrimidine-5-carboxamide To a solution of Intermediate 8 (214 mg, 0.5 mmol), TBTU (241 mg, 0.75 mmol) and DIPEA (260 µL, 1.5 mmol) in DMF (10 mL) was added 2-hydroxyethylamine (92 µL, 1.5 mmol). The reaction mixture was stirred for 6 h, then concentrated to dryness in vacuo. The residue was purified by silica gel chromatography (DCM:MeOH 9:1, then DCM:MeOH:NH$_3$-MeOH 100:10:1) to provide the title compound (166 mg, 70%) as a yellow solid. $^{13}$C NMR (75 MHz, DMSO-d$_6$) δ 161.7, 160.5, 158.4, 155.2, 154.6, 154.5, 134.3, 133.3, 121.6 (2C), 114.4, 113.5 (2C), 108.8, 59.3, 55.1, 48.1 (2C), 43.0 (2C), 42.7. MS m/z (%) 472 [M+H]$^+$.

Intermediate 10

5-Amino-3-methylisoxazolo[4,5-d]pyrimidin-7-ol

4M HCl in 1,4-dioxane (14.7 mL, 59.1 mmol) was added dropwise to a solution of cyanamide (1.86 g, 44.3 mmol) in 1,4-dioxane (5 mL). A thick white precipitate formed. The reaction mixture was left to stir for 1 h, then evaporated to dryness. The resulting crude material (2.03 g, 17.6 mmol) was treated with ethyl 4-amino-3-methylisoxazole-5-carboxylate (3.0 g, 17.6 mmol) in diethylene glycol dimethyl ether (10 mL), then the reaction mixture was heated at 180° C. (reflux) and maintained at this temperature for 5 minutes. A brown tar formed on the bottom of the flask. The reaction mixture was cooled to r.t. and the solvent was decanted away. The resulting crude material (3.70 g, 17 mmol) was treated with 2M NaOH in water (15 mL, 150 mmol) and heated at 70° C., then cooled to r.t. The reaction mixture was cooled in an ice-bath, and acidified to pH 2 with concentrated HCl. The resulting precipitate was collected, washed with diethyl ether, and dried in vacuo, to give the title compound (2.7 g, 93%). $\delta_H$ (400 MHz, DMSO-$d_6$) 11.41 (s, 1H), 6.54 (s, 2H), 2.33 (s, 3H).

Intermediate 11

7-[(2S)-2-Ethylpiperazin-1-yl]-3-methylisoxazolo[4,5-d]pyrimidin-5-amine dihydrochloride Intermediate 10 (2.70 g, 16 mmol) was slurried in phosphorus oxychloride (33 mL) and DIPEA (5.3 mL) was added. The mixture was heated at reflux for 5 h. Upon cooling, the reaction mixture was concentrated in vacuo. The brown oil was partitioned between EtOAc and water. The organic layer was dried over $Na_2SO_4$ and concentrated. The resulting crude brown oil was dissolved in DMF (10 mL) and DIPEA (1.3 mL) was added, followed by (S)-tert-butyl 3-ethylpiperazine-1-carboxylate (0.96 g, 4.17 mmol). The reaction mixture was stirred at 70° C. overnight. The resulting solution was concentrated in vacuo, and the residue was purified by silica gel chromatography (gradient 40-100% EtOAc in isohexane). The resulting crude material was dissolved in EtOH, then 4M HCl in 1,4-dioxane (10 mL) was added. The reaction mixture was stirred for 2 h, then concentrated in vacuo, to give the title compound (1.0 g, 19% overall) as a sticky brown solid. LCMS (ES+) MH$^+$ 263, RT 0.76 minutes (method 1).

Intermediate 12

Ethyl 1-methyl-4-nitropyrazole-3-carboxylate

Iodomethane (0.75 mL, 12 mmol) was added to a suspension of ethyl 4-nitro-1H-pyrazole-3-carboxylate (2 g, 10.80 mmol) and potassium carbonate (2.24 g, 16.2 mmol) in acetonitrile (50 mL). The reaction mixture was stirred overnight, then concentrated in vacuo. The residue was partitioned between DCM and brine, then separated. The organic layer was passed through a phase separator cartridge, then evaporated. The resulting crude material was purified by silica gel chromatography (gradient 5-30% EtOAc in isohexane). The title compound (1.31 g, 60.9%) was obtained as a white solid. $\delta_H$ (400 MHz, DMSO-$d_6$) 8.94 (s, 1H), 4.36 (q, 2H, J 7.1 Hz), 3.95 (s, 3H), 1.30 (t, 3H, J 7.1 Hz).

Intermediate 13

Ethyl 4-amino-1-methylpyrazole-3-carboxylate

Tin(II) chloride dihydrate (7.42 g, 32.9 mmol) was added to a solution of Intermediate 12 (1.31 g, 6.58 mmol) in EtOH (50 mL). The reaction was heated at 50° C. with stirring for 3.5 h, then cooled to room temperature and concentrated in vacuo. The residue was diluted with DCM and treated with 2M aqueous NaOH solution. A viscous thick precipitate formed. The mixture was filtered through celite, and the two layers were separated. The aqueous layer was extracted with DCM (twice). The combined organic layers were passed through a phase separator cartridge, then evaporated. The resulting crude material was purified by silica gel chromatography (gradient 25-75% EtOAc in isohexane). The title compound (0.32 g, 29%) was isolated as a dark blue/black oil. $\delta_H$ (400 MHz, DMSO-$d_6$) 7.12 (s, 1H), 4.66 (s, 2H), 4.23 (q, 2H, J 7.1 Hz), 3.76 (s, 3H), 1.27 (t, 3H, J 7.1 Hz).

Intermediate 14

5-Amino-2-methylpyrazolo[4,3-d]pyrimidin-7-ol

Prepared from Intermediate 13 (0.32 g, 1.9 mmol), 4M HCl in 1,4-dioxane (1.6 mL, 6.4 mmol), cyanamide (200 mg, 4.76 mmol), 1,4-dioxane (5 mL), diethylene glycol dimethyl ether (10 mL) and 2M aqueous NaOH solution (15 mL) according to the procedure described for Intermediate 10, except that during the final step the title compound precipitated from the aqueous solution at pH 7. The title compound (162 mg, 52%) was obtained as a brown solid. $\delta_H$ (400 MHz, DMSO-$d_6$) 10.59 (s, 1H), 7.70 (s, 1H), 5.93 (s, 2H), 3.94 (s, 3H).

Intermediate 15 tert-Butyl (3S)-4-(5-amino-2-methylpyrazolo[4,3-d]pyrimidin-7-yl)-3-methylpiperazine-1-carboxylate DBU (0.22 mL, 1.5 mmol) was added to a suspension of Intermediate 14 (162 mg, 0.98 mmol), (S)-tert-butyl 3-methylpiperazine-1-carboxylate (218 mg, 1.09 mmol) and PyBOP (679 mg, 1.30 mmol) in MeCN (5 mL). The reaction mixture was heated at 60° C. for 4 days, then cooled to room temperature and concentrated in vacuo. The residue was partitioned between EtOAc and water, filtered to remove a small quantity of insoluble material, and separated. The organic layer was washed with brine, dried with $MgSO_4$ and evaporated. The resulting crude material was purified by NH-silica gel chromatography (gradient 50-100% EtOAc in isohexane). The title compound (61 mg, 17.9%) was isolated as a colourless oil. $\delta_H$ (400 MHz, DMSO-$d_6$) 7.75 (s, 1H), 5.52 (s, 2H), 3.96-4.04 (m, 2H), 4.00 (s, 3H), 3.81-3.86 (m, 1H), 3.09-3.30 (m, 3H), 3.06-3.21 (m, 1H), 1.43 (s, 9H), 1.17 (d, 3H, J 6.7 Hz).

Intermediate 16

2-Methyl-7-[(2S)-2-methylpiperazin-1-yl]pyrazolo[4,3-d]pyrimidin-5-amine

4M HCl in 1,4-dioxane (2 mL) was added to Intermediate 15 (61 mg, 0.18 mmol). The reaction mixture was stirred for 2.5 h, then concentrated in vacuo. The residue was dissolved in water, then washed with DCM (twice). The aqueous solution was basified to pH 14 with 2M aqueous NaOH solution, then extracted with 10% MeOH in DCM (5 times). The organic extracts were combined, passed through a phase separator cartridge and evaporated, to give the title compound (36 mg, 83%) as a brown gum. LCMS (ES+) [M+H]$^+$ 248, RT 0.55 minutes (method 1).

Intermediate 17

Methyl 4-amino-2,5-dimethyl-2H-pyrazole-3-carboxylate

To a solution of methyl 1,3-dimethyl-4-nitro-1H-pyrazole-5-carboxylate (0.3 g, 1.5 mmol) in MeOH (3 mL) was added Raney nickel (50% in water, 20 mg). The solution was stirred overnight under a hydrogen atmosphere. The reaction mixture was filtered through Celite, and washed with MeOH. The solvent was evaporated in vacuo, yielding the title compound (0.206 g, 81%), an off-white solid. $^{13}$C NMR (CDCl$_3$, 75 MHz) δ 160.5, 133.8, 130.5, 117.1, 50.9, 39.0, 9.8. MS (m/z) 170 [M+H]$^+$.

Intermediate 18

1,3-Dimethyl-5-thioxo-4H-pyrazolo[4,3-d]pyrimidin-7-one

To a solution of Intermediate 17 (206 mg, 1.2 mmol) in acetone (10 mL) was added benzoyl isothiocyanate (172 µL, 1.3 mmol). The solution was stirred for 1 h, then extracted with EtOAc and brine. The organic layer was dried over MgSO$_4$. The solvents were evaporated in vacuo. The resulting crude material was dissolved in acetone (15 mL), MeOH (15 mL) and water (2.5 mL). Potassium carbonate (330 mg, 2.4 mmol) was added, and the mixture was stirred at reflux for 2 h. The reaction mixture was cooled and placed in an ice bath. Acetic acid was added until pH 7. The precipitated solids were isolated by filtration and dried, to give the title compound (140 mg, 26% overall) as a yellow solid. $^{13}$C NMR (DMSO-d$_6$, 75 MHz) δ 174.1, 153.8, 133.0, 129.8, 123.4, 38.6, 11.7. MS (m/z) 197 [M+H]$^+$.

Intermediate 19

1-Methyl-5-thioxo-4H-pyrazolo[4,3-d]pyrimidin-7-one

Prepared from methyl 4-amino-1-methyl-1H-pyrazole-5-carboxylate (1 g, 6.4 mmol) according to the procedure described for Intermediate 18 to give the title compound (289 mg, 25%) as a yellow solid. $^{13}$C NMR (DMSO-d$_6$, 75 MHz) δ 173.4, 152.8, 130.8, 123.7, 122.1, 38.3. MS (m/z) 183 [M+H]$^+$.

Intermediate 20

1,3-Dimethyl-5-(methylsulfanyl)-6H-pyrazolo[4,3-d]pyrimidin-7-one

To a solution of Intermediate 18 (131 mg, 0.67 mmol) in EtOH (3 mL) was added aqueous NaOH solution (1.73N, 782 µL), followed by iodomethane (44 µL, 0.70 mmol). The reaction mixture was stirred at r.t. and monitored by TLC. After completion, a 2N solution of sulfuric acid was added dropwise until pH 7. The mixture was cooled (0° C.), and the precipitated solids were isolated by filtration and dried, to give the title compound (130 mg, 33%) as a yellow solid. $^{13}$C NMR (DMSO-d$_6$, 75 MHz) δ 154.2, 153.0, 139.2, 138.1, 123.6, 37.8, 13.0, 10.4. MS (m/z) 211 [M+H]$^+$.

Intermediate 21

1-Methyl-5-(methylsulfanyl)-6H-pyrazolo[4,3-d]pyrimidin-7-one

Prepared from Intermediate 19 (289 mg, 1.6 mmol) according to the procedure described for Intermediate 20 to give the title compound (243 mg, 78%) as a yellow solid. $^{13}$C NMR (DMSO-d$_6$, 75 MHz) δ 153.9, 140.1, 131.3, 123.7, 123.3, 38.4, 13.1. MS (m/z) 197 [M+H]$^+$.

Intermediates 22 to 31

To a cooled (ice bath) solution of the appropriate amine (1 mmol) in THF (50 mL) was added pyridine (1.1 equivalents), followed by phenyl chloroformate (1 equivalent) dropwise. The reaction mixture was allowed to warm to room temperature. When LCMS confirmed complete conversion of the amine to the desired carbamate, the reaction mixture was quenched with water. The title compound was then either collected by filtration, or extracted into DCM, phase separated and concentrated in vacuo, and used without further purification.

| | | LCMS Data | |
|---|---|---|---|
| Int. Name | RT | [M + H]$^+$ | Method |
| 22 Phenyl N-(6-ethoxy-2-methylpyridin-3-yl)carbamate | 1.45 | 273 | 1 |
| 23 Phenyl N-[2-methyl-4-(trifluoromethoxy)phenyl]-carbamate | 2.26 | 312 | 1 |
| 24 Phenyl N-(2,6-dimethoxypyridin-3-yl)carbamate | 1.44 | 275 | 1 |
| 25 Phenyl N-[6-(3,3-difluoroazetidin-1-yl)-2-methyl-pyridin-3-yl]carbamate | 1.34 | 320 | 1 |
| 26 Phenyl N-(4-methoxy-2-methylphenyl)carbamate | 1.87 | 258 | 2 |
| 27 Phenyl N-(4-methoxy-3-methylphenyl)carbamate | 2.02 | 258 | 2 |
| 28 Phenyl N-[6-(dimethylamino)-2-methylpyridin-3-yl]-carbamate | 1.79 | 272 | 2 |
| 29 Phenyl N-[6-(azetidin-1-yl)-2-methylpyridin-3-yl]-carbamate | 1.58 | 284 | 2 |
| 30 Phenyl N-[5-methoxy-6-(trifluoromethyl)pyridin-2-yl]carbamate | 2.14 | 313 | 2 |
| 31 Phenyl N-(4-isopropoxy-2-methylphenyl)carbamate | 2.20 | 286 | 2 |

Intermediate 32

2,4-Dichloro-5-methylpyrrolo[3,2-d]pyrimidine

Iodomethane (0.98 mL, 16 mmol) was added to a suspension of 2,4-dichloro-5H-pyrrolo[3,2-d]pyrimidine (3 g, 15.8 mmol) and cesium carbonate (5.14 g, 15.8 mmol) in DMF (50 mL). The reaction mixture was stirred for 1.5 h, then water was added. The resulting thick white precipitate was filtered off, then washed with water and isohexane. The residue was concentrated by evaporation to provide the title compound (2.58 g, 81%) as a white solid. LCMS (ES+) [M+H]$^+$ 202, 204, RT 1.13 minutes (method 1).

Intermediate 33 tert-Butyl (3S)-4-(2-chloro-5-methylpyrrolo[3,2-d]pyrimidin-4-yl)-3-methylpiperazine-1-carboxylate DIPEA (4.5 mL, 26 mmol) was added to a solution of Intermediate 32 (2.58 g, 12.76 mmol) and (S)-tert-butyl 3-methylpiperazine-1-carboxylate (2.67 g, 13.3 mmol) in DMF (50 mL). The reaction mixture was heated to 110° C. and stirred for 4 days. The reaction mixture was cooled to room temperature and concentrated in vacuo. The residue was dissolved in EtOAc (50 mL), washed with saturated aqueous NaHCO$_3$ solution (50 mL) and brine (2×50 mL), then dried over Na$_2$SO$_4$ and evaporated. The crude residue was purified by silica gel chromatography (gradient of 30-70% EtOAc in isohexane) to provide the title compound (3.93 g, 84%) as a brown viscous foaming gum. LCMS (ES+) [M+H]$^+$ 366, 368, RT 1.51 minutes (method 1).

Intermediate 34 tert-Butyl (3S)-4-{2-[(4-methoxyphenyl)methyl-amino]-5-methylpyrrolo[3,2-d]pyrimidin-4-yl}-3-methylpiperazine-1-carboxylate A solution of Intermediate 33 (3.93 g, 10.75 mmol) in 4-methoxybenzylamine (7 mL) was heated at 170° C. under microwave irradiation for 2 h. The reaction mixture was diluted with EtOAc (50 mL) and water (50 mL), then separated. The organic phase was washed with water (50 mL) and brine (50 mL), then dried (Na$_2$SO$_4$) and evaporated onto silica. The crude residue was purified by NH-silica gel (gradient of 10-45% EtOAc in isohexane) to provide the title compound (2.64 g, 53%) as a cream-coloured foaming gum. LCMS (ES+) [M+H]$^+$ 467, RT 1.60 minutes (method 1).

Intermediate 35

5-Methyl-4-[(2S)-2-methylpiperazin-1-yl]pyrrolo[3,2-d]pyrimidin-2-amine bis(trifluoroacetate)

Intermediate 34 (2.64 g, 5.65 mmol) was dissolved in TFA (50 mL) and the reaction mixture was heated at 50° C. overnight with stirring. The reaction mixture was cooled to room temperature and concentrated in vacuo. The resulting dark pink/brown sticky gum was triturated with diethyl ether and filtered, then washed with diethyl ether and concentrated by evaporation, to provide the title compound (2.80 g, quantitative) as a cream-coloured solid. LCMS (ES+) [M+H]$^+$ 247, RT 0.90 minutes (method 1).

Intermediate 36 tert-Butyl (3S)-3-methyl-4-[1-methyl-5-(methylsulfanyl)pyrazolo[4,3-d]pyrimidin-7-yl]-piperazine-1-carboxylate Intermediate 21 (3 g, 15.3 mmol) was suspended in POCl$_3$ (10.6 g, 8.00 mL, 68.9 mmol) with N,N-diethylaniline (1.15 g, 1.23 mL, 7.72 mmol). The reaction mixture was heated at 110° C. for 1 h, then cooled and stirred at r.t. overnight. The residue was concentrated to dryness, then partitioned between DCM and brine. The organic layers were phase separated, then concentrated. The resulting sticky yellow gum was taken up in 2-methyltetrahydrofuran (60 mL), then (S)-tert-butyl 3-methylpiperazine-1-carboxylate (1.9 g, 9.32 mmol) and DIPEA (1.21 g, 1.63 mL, 9.32 mmol) were added. The reaction mixture was heated at reflux for 4 days. The reaction was partitioned into water, then the organic layers were dried over Na$_2$SO$_4$ and concentrated in vacuo. The resulting yellow semi-solid was purified by column chromatography (SiO$_2$, 100% EtOAc) to give the title compound (1.5 g, 26%) as a yellow solid. LCMS (ES+) [M+H]$^+$ 379, RT 2.09 minutes (method 1).

Intermediate 37 tert-Butyl (3S)-3-methyl-4-[1-methyl-5-(methylsulfonyl)pyrazolo[4,3-d]pyrimidin-7-yl]-piperazine-1-carboxylate Intermediate 36 (1.5 g, 4.0 mmol) in DCM (100 mL) was treated with MCPBA (2.0 g, 7.9 mmol). The reaction mixture was stirred overnight, then partitioned between DCM and saturated aqueous NaHCO$_3$ solution. The organic layers were separated and dried over Na$_2$SO$_4$, then concentrated in vacuo, to give the title compound (1.38 g, 85%) as a yellow solid. LCMS (ES+) [M+H]$^+$ 411, RT 1.57 minutes (method 1).

Intermediate 38 tert-Butyl (3S)-4-(5-amino-1-methylpyrazolo[4,3-d]pyrimidin-7-yl)-3-methylpiperazine-1-carboxylate Intermediate 37 (1.38 g, 3.36 mmol) was dissolved in 1,4-dioxane (20 mL) and loaded into a pressure vessel with 15% aqueous NH$_4$OH solution (20 mL). The mixture was heated at 100° C. for 2 h, then at 110° C. and left for 4 h. The reaction mixture was stirred at r.t. overnight, then heated again with fresh ammonia solution for 2 h at 110° C. The reaction mixture was concentrated, then partitioned between DCM and water. The organic layers were phase separated and concentrated. The residue was purified by column chromatography (SiO$_2$, gradient of 100% EtOAc to 20% MeOH in EtOAc) to give the title compound (450 mg, 38.5%). LCMS (ES+) [M+H]$^+$ 348, RT 1.41 minutes (method 1).

Intermediate 39

1-Methyl-7-[(2S)-2-methylpiperazin-1-yl]pyrazolo[4,3-d]pyrimidin-5-amine dihydrochloride Intermediate 38 (5 g, 14.39 mmol) in 4N HCl in dioxane (100 mL) was stirred overnight at r.t. The resultant solid was collected by filtration to yield the title compound (4.5 g, 98%) as a buff-coloured solid. LCMS (ES+) [M+H]$^+$ 248, RT 0.61 minutes (method 1).

Intermediate 40 tert-Butyl (3S)-4-[1,3-dimethyl-5-(methylsulfanyl)-1H-pyrazolo[4,3-d]pyrimidin-7-yl]-3-methylpiperazine-1-carboxylate To a stirred solution of Intermediate 20 (1.3 g, 6.19 mmol) in POCl$_3$ (20 mL) were added DMF (0.1 mL) and pyridine (0.1 mL). The reaction mixture was heated at 100° C. for 2 h, then evaporated in vacuo. The crude residue was neutralized with saturated aqueous NaHCO$_3$ solution. The aqueous layer was extracted with EtOAc (2×20 mL), then the organic layer was dried over anhydrous Na$_2$SO$_4$ and concentrated in vacuo. The residue was taken up in EtOH (25 mL) in a sealed tube, then (S)-tert-butyl 3-methylpiperazine-1-carboxylate (1.41 g, 7.05 mmol) and DIPEA (2.3 mmol, 14.1 mmol) were added. The reaction mixture was heated at 100° C. for 16 h, then cooled to r.t. and concentrated in vacuo. The crude residue was purified by column chromatography (normal phase; silica 100-200 mesh; 50% EtOAc in hexanes) to afford the title compound (1.3 g, 84%) as a yellow solid. LCMS (ES+) [M+H]$^+$ 393, RT 3.01 minutes (method 2).

Intermediate 41 tert-Butyl (3S)-4-[1,3-dimethyl-5-(methylsulfonyl)-1H-pyrazolo[4,3-d]pyrimidin-7-yl]-3-methylpiperazine-1-carboxylate Prepared from Intermediate 40 (1.1 g, 2.8 mmol) according to the procedure described for Intermediate 37 to give the title compound (1.1 g, 93%) as a pale yellow solid. LCMS (ES+) [M+H]$^+$ 425, RT 2.41 minutes (method 2).

Intermediate 42 tert-Butyl (3S)-4-(5-amino-1,3-dimethyl-1H-pyrazolo[4,3-d]pyrimidin-7-yl)-3-methylpiperazine-1-carboxylate To a stirred solution of Intermediate 41 (1 g, 2.35 mmol) in 1,4-dioxane (50 mL) in a sealed tube was added 15% aqueous NH$_4$OH solution (50 mL). The mixture was cooled to −20° C. and ammonia gas was bubbled through for 20 minutes. The reaction mixture was heated at 100° C. for 16 h. After cooling, the white solid that had precipitated was filtered and dried under vacuum to afford the title compound (0.60 g, 71%) as a white solid. LCMS (ES+) [M+H]$^+$ 362, RT 2.29 minutes (method 2).

Intermediate 43

1,3-Dimethyl-7-[(2S)-2-methylpiperazin-1-yl]-1H-pyrazolo[4,3-d]pyrimidin-5-amine To a stirred solution of Intermediate 42 (0.45 g, 1.24 mmol) in DCM (2 mL) was added TFA (2 mL) at 0° C. The reaction mixture was stirred at r.t. for 30 minutes, then concentrated in vacuo. The crude residue was co-evaporated with 7N ammonia in methanol to afford the title compound (quantitative), which was used without further purification. LCMS (ES+) [M+H]$^+$ 262, RT 1.93 minutes (method 2).

Example 1

Methyl 2-amino-4-{4-[(4-methoxyphenyl)carbamoyl]piperazin-1-yl}thieno[3,4-d]-pyrimidine-5-carboxylate To a suspension of Intermediate 2 (117 mg, 0.4 mmol) in 1,4-dioxane (12 mL) was added 4-methoxyphenyl isocyanate (63 μL, 0.48 mmol) at room temperature. The reaction mixture was stirred for 3 h, then partitioned between DCM and water. The organic phase was dried with anhydrous MgSO$_4$, then the solvent was evaporated in vacuo. The residue was purified by silica gel chromatography (DCM:MeOH 15:1) to provide the title compound (160 mg, 90%) as a yellow solid. δ$_H$ (300 MHz, CDCl$_3$+CD$_3$OD) 7.33 (s, 1H), 7.23 (d, 2H, J 9.0 Hz), 6.82 (d, 2H, J 9.0 Hz), 3.92 (s, 3H), 3.76 (s, 3H), 3.75 (m, 4H), 3.62 (m, 4H). MS m/z (%) 443 [M+H]$^+$.

Example 2

Methyl 2-amino-4-{4-[(4-methoxy-2-methylphenyl)carbamoyl]piperazin-1-yl}thieno[3,4-d]pyrimidine-5-carboxylate Prepared from Intermediate 2 (88 mg, 0.3 mmol) and 4-methoxy-2-methylphenyl isocyanate (49 μL, 0.36 mmol) according to the procedure described for Example 1 to give the title compound (81 mg, 59%) as a yellow solid. δ$_H$ (300 MHz, CDCl$_3$+CD$_3$OD) 7.35 (s, 1H), 7.04 (m, 1H), 6.68 (m, 2H), 3.94 (s, 3H), 3.76 (s, 3H), 3.75 (m, 4H), 3.62 (m, 4H), 2.22 (s, 3H). MS m/z (%) 457 [M+H]$^+$.

Example 3

Methyl 2-amino-4-(4-{[4-(dimethylamino)phenyl]carbamoyl}piperazin-1-yl)thieno[3,4-d]pyrimidine-5-carboxylate Prepared from Intermediate 2 (70 mg, 0.24 mmol) and 4-(dimethylamino)phenyl isocyanate (41 mg, 0.25 mmol) according to the procedure described for Example 1 to give the title compound (58 mg, 53%) as a yellow solid. $^{13}$C NMR (75 MHz, CDCl$_3$+CD$_3$OD) δ 165.2, 164.05, 162.5, 160.4, 159.0, 151.4, 132.8, 130.0, 126.8 (2C), 121.4, 118.1, 117.4 (2C), 56.2, 51.9 (2C), 47.0 (2C), 44.7 (2C). MS m/z (%) 456 [M+H]$^+$.

Example 4

Ethyl 2-amino-4-{4-[(4-methoxyphenyl)carbamoyl]piperazin-1-yl}thieno[3,4-d]-pyrimidine-5-carboxylate To a solution of Example 1 (160 mg, 0.36 mmol) in absolute EtOH (10 mL) was added sodium hydride (60% in mineral oil, 15 mg, 0.36 mmol) under nitrogen. The reaction mixture was stirred at r.t. for 18 h under nitrogen, then partitioned between DCM and water and separated. The aqueous layer was extracted with DCM (twice). The combined organic phases were dried with anhydrous MgSO$_4$, concentrated, and purified by silica gel chromatography (DCM:MeOH 10:1), to provide the title compound (85 mg, 52%) as a yellow solid. $^{13}$C NMR (75 MHz, CDCl$_3$) δ 160.9, 160.4, 158.1, 156.1, 155.8, 153.8, 132.0, 127.6, 122.8 (2C), 117.6, 114.3, 114.2 (2C), 62.2, 55.6, 48.5 (2C), 43.6 (2C), 14.4. MS m/z (%) 457 [M+H]$^+$.

Example 5

4-(2-Aminothieno[3,4-d]pyrimidin-4-yl)-N-(4-methoxy-2-methylphenyl)piperazine-1-carboxamide Intermediate 6 was suspended in DMF (10 mL) and treated with 4-methoxy-2-methylphenyl isocyanate (27 μL, 0.2 mmol). The solution turned clear and the reaction mixture was stirred at room temperature for 2 h. The reaction mixture was concentrated in vacuo, and purified by silica gel chromatography (DCM:MeOH 19:1, then DCM:MeOH:NH$_3$-MeOH 100:10:1), to provide the title compound (45 mg, 55%) as a yellow solid. δ$_H$ (300 MHz, CDCl$_3$+CD$_3$OD) 8.26 (d, 1H, J 3.0 Hz), 7.08-7.23 (m, 2H), 6.69-6.77 (m, 2H), 4.23 (m, 4H), 3.79 (m, 4H), 3.77 (s, 3H), 2.24 (s, 3H). MS m/z (%) 399 [M+H]$^+$.

Example 6

4-(2-Aminothieno[3,4-d]pyrimidin-4-yl)-N-[4-(dimethylamino)phenyl]piperazine-1-carboxamide To a suspension of Intermediate 7 (0.3 g, 1.8 mmol), piperazine (0.309 g, 3.6 mmol) and BOP (1.03 g, 2.3 mmol) in DMF (20 mL) was added DBU (0.4 mL, 2.7 mmol). The reaction mixture was stirred at room temperature for 16 h. The solvent was evaporated in vacuo and the residue was purified by silica gel chromatography (DCM:MeOH:NH$_3$-MeOH 100:10:1). The resulting crude material (70 mg, 0.3 mmol) was suspended in DMF (2 mL) and 4-(dimethylamino)phenyl isocyanate (51 mg, 0.31 mmol) was added. The reaction mixture was stirred at r.t. for 2 h, then concentrated in vacuo and purified by silica gel chromatography (DCM:MeOH 19:1, then DCM:MeOH:NH$_3$-MeOH 100:10:1), to provide the title compound (22 mg, 18% overall) as a white solid. $^{13}$C NMR (75 MHz, CDCl$_3$+CD$_3$OD) δ 158.9, 158.0, 155.5, 153.6, 146.7, 130.2, 124.0, 122.1 (2C), 117.2, 112.9 (2C), 105.3, 45.8 (2C), 43.0 (2C), 40.8 (2C). MS m/z (%) 398 [M+H]$^+$.

Example 7

2-Amino-4-{4-[(4-methoxyphenyl)carbamoyl]piperazin-1-yl}thieno[3,4-d]pyrimidine-5-carboxamide Prepared from Intermediate 8 (98 mg, 0.23 mmol), TBTU (110 mg, 0.34 mmol), concentrated ammonia solution (70 μL, 0.91 mmol) and DIPEA (59 μL, 0.343 mmol) in DMF (4 mL) according to the procedure described for Intermediate 9 to give the title compound (20 mg, 20%) as a yellow solid. $δ_H$ (300 MHz, DMSO-d$_6$) 8.45 (m, 1H), 7.96 (s, 1H), 7.81 (s, 1H), 7.33 (d, 2H, J 6.9 Hz), 7.21 (s, 1H), 6.81 (d, 2H, J 6.9 Hz), 6.44 (s, 2H), 3.70 (s, 3H), 3.56 (m, 8H). MS m/z (%) 428 [M+H]$^+$.

Example 8

2-Amino-N-methoxy-4-{4-[(4-methoxyphenyl)carbamoyl]piperazin-1-yl}-N-methyl-thieno[3,4-d]pyrimidine-5-carboxamide Prepared from Intermediate 8 (129 mg, 0.3 mmol), TBTU (145 mg, 0.45 mmol), DIPEA (207 μL, 1.2 mmol) and N,O-dimethylhydroxylamine hydrochloride (35 mg, 0.36 mmol) in DMF (4 mL) according to the procedure described for Intermediate 9 to give the title compound (73 mg, 51%) as a yellow solid. $δ_H$ (300 MHz, CDCl$_3$+CD$_3$OD) 7.29 (s, 1H), 7.27 (d, 2H, J 6.6 Hz), 6.82 (d, 2H, J 6.6 Hz), 3.92 (m, 4H), 3.67 (m, 10H), 3.41 (s, 3H). MS m/z (%) 472 [M+H]$^+$.

Example 9

4-[2-Amino-5-(4,5-dihydro-1,3-oxazol-2-yl)thieno[3,4-d]pyrimidin-4-yl]-N-(4-methoxyphenyl)piperazine-1-carboxamide A mixture of Intermediate 9 (95 mg, 0.2 mmol), copper (II) trifluoromethanesulfonate (22 mg, 0.06 mmol) and DIC (38 μL, 0.24 mmol) in anhydrous DMF (4 mL) was stirred at room temperature for 16 h, then heated at 110° C. for 20 minutes. The reaction mixture was concentrated, then purified by silica gel chromatography (DCM:MeOH 19:1, then DCM:MeOH:NH$_3$-MeOH 100:10:1), to provide the title compound (42 mg, 46%) as a brown solid. $^{13}$C NMR (75 MHz, DMSO-d$_6$) δ 162.0, 159.1, 158.1, 155.2, 154.9, 154.5, 133.2, 126.9, 121.6 (2C), 114.9, 113.5 (2C), 109.1, 68.4, 55.1, 55.0, 48.2 (2C), 43.2 (2C). MS m/z (%) 454 [M+H]$^+$.

Example 10

(3S)-4-(5-Amino-3-methyl[1,2]oxazolo[4,5-d]pyrimidin-7-yl)-N-(6-ethoxy-2-methylpyridin-3-yl)-3-ethylpiperazine-1-carboxamide Intermediate 11 (70 mg, 0.21 mmol) was suspended in MeCN (5 mL) and Intermediate 22 (56.86 mg, 0.21 mmol) was added, followed by DIPEA (73 μL, 0.42 mmol). The reaction mixture was stirred at 70° C. for 1 h. Upon cooling, the reaction mixture was concentrated in vacuo, and the residue was purified by HPLC. Upon freeze-drying, the title compound (30 mg, 32.61%) was obtained as a white solid. $δ_H$ (400 MHz, DMSO-d$_6$) 8.15 (s, 1H), 7.41 (d, 1H, J 8.6 Hz), 6.59 (d, 1H, J 8.4 Hz), 6.21 (s, 2H), 4.45-4.80 (m, 2H), 4.26 (q, 2H, J 7.0 Hz), 4.13-4.21 (m, 2H), 3.18-3.25 (m, 1H), 3.01-3.11 (m, 1H), 2.37 (s, 3H), 2.27 (s, 3H), 1.77-1.69 (m, 2H), 1.33-1.28 (m, 3H), 0.84-0.90 (m, 3H). LCMS (ES+) MH$^+$ 441, RT 1.80 minutes (method 2).

Example 11

(3S)-4-(5-Amino-3-methyl[1,2]oxazolo[4,5-d]pyrimidin-7-yl)-3-ethyl-N-[2-methyl-4-(trifluoromethoxy)phenyl]piperazine-1-carboxamide Prepared from Intermediate 11 (70 mg, 0.21 mmol), Intermediate 23 (65.01 mg, 0.21 mmol) and DIPEA (0.13 mL, 0.42 mmol) in MeCN (5 mL) according to the procedure described for Example 10 to give the title compound (100 mg, 100%) as a white solid. $δ_H$ (400 MHz, DMSO-d$_6$) 8.23 (s, 1H), 7.30 (m, 1H), 7.18 (m, 2H), 6.21 (s, 2H), 4.50-4.85 (m, 2H), 4.20-4.13 (m, 2H), 3.18-3.29 (m, 1H), 3.01-3.16 (m, 1H), 2.37 (s, 3H), 2.22 (s, 3H), 1.65-1.86 (m, 2H), 0.87 (t, 3H, J 7.3 Hz). LCMS (ES+) MH$^+$ 480, RT 2.30 minutes (method 2).

Example 12

(3S)-4-(5-Amino-3-methyl[1,2]oxazolo[4,5-d]pyrimidin-7-yl)-N-(2,6-dimethoxypyridin-3-yl)-3-ethylpiperazine-1-carboxamide Prepared from Intermediate 11 (70 mg, 0.21 mmol), Intermediate 24 (57 mg, 0.21 mmol) and DIPEA (73 μL, 0.42 mmol) in MeCN (5 mL) according to the procedure described for Example 10 to give the title compound (40.4 mg, 44%) as a white solid. $δ_H$ (400 MHz, DMSO-d$_6$) 7.83 (s, 1H), 7.62 (d, 1H, J 8.2 Hz), 6.35 (d, 1H, J 8.2 Hz), 6.20 (s, 2H), 4.50-4.81 (m, 2H), 4.10-4.20 (m, 2H), 3.89 (s, 3H), 3.85 (s, 3H), 3.14-3.24 (m, 1H), 2.97-3.11 (m, 1H), 2.36 (s, 3H), 1.63-1.83 (m, 2H), 0.87 (t, 3H, J 7.3 Hz). LCMS (ES+) MH$^+$ 443, RT 1.87 minutes (method 2).

Example 13

(3S)-4-(5-Amino-2-methyl-2H-pyrazolo[4,3-d]pyrimidin-7-yl)-3-methyl-N-[2-methyl-4-(trifluoromethoxy)phenyl]piperazine-1-carboxamide DIPEA (0.03 mL, 0.2 mmol) was added to a suspension of Intermediate 16 (36 mg, 0.15 mmol) and Intermediate 23 (65 mg, 0.21 mmol) in MeCN (5 mL). The reaction mixture was stirred overnight, then concentrated in vacuo. The residue was diluted with DCM and washed with brine, then passed through a phase separator cartridge and evaporated. The crude material was purified by NH-silica gel chromatography (gradient 1-10% MeOH in EtOAc). The residue was freeze-dried from MeCN/water over 3 days to give the title compound (23.9 mg, 29%) as a white powder. $δ_H$ (400 MHz, DMSO-d$_6$) 8.17 (s, 1H), 7.78 (s, 1H), 7.32 (d, 1H, J 8.7 Hz), 7.21-7.23 (m, 1H), 7.13-7.17 (m, 1H), 5.65 (s, 2H), 5.36 (br m, 2H), 4.14-4.19 (m, 1H), 4.03 (s, 3H), 3.99-4.01 (m, 1H), 3.38 (br m, 1H), 3.26-3.27 (m, 1H), 3.03-3.12 (m, 1H), 2.23 (s, 3H), 1.26 (d, 3H, J 6.6 Hz). LCMS (ES+) [M+H]+ 465, RT 1.88 minutes (method 2).

Example 14

(3S)-4-(5-Amino-1,3-dimethyl-1H-pyrazolo[4,3-d]pyrimidin-7-yl)-N-[6-(3,3-difluoroazetidin-1-yl)-2-methylpyridin-3-yl]-3-methylpiperazine-1-carboxamide To a suspension of Intermediate 20 (125 mg, 0.59 mmol) in phosphorus oxychloride (1.2 mL) was added N,N-dimethylaniline (25 µL). The suspension was stirred at 110° C. and monitored by TLC. After completion (the suspension turned into a solution), the reaction mixture was cooled and evaporated in vacuo. The residue was extracted with EtOAc and brine, and the organic solvent was dried over MgSO$_4$. The resulting crude material (90 mg, 0.39 mmol) was dissolved in THF and treated with triethylamine (82 µL, 0.59 mmol), followed by (S)-tert-butyl 3-methylpiperazine-1-carboxylate (87 mg, 0.43 mmol). The reaction mixture was stirred for 24 h at r.t., after which time the mixture was evaporated in vacuo, then extracted using DCM and brine. The crude residue was purified using silica gel chromatography (EtOAc:cyclohexane 4:1). The resulting isolated solids (124 mg, 0.33 mmol) were dissolved in DCM (4 mL) and MCPBA (165 mg, 0.67 mmol) was added at 0° C. The reaction mixture was stirred at r.t. for 2 h, whereupon 2N aqueous Na$_2$SO$_3$ solution (3 mL) was added. The mixture was extracted using EtOAc and 2N aqueous NaOH solution, then brine. The organic solvents were dried over MgSO$_4$, then evaporated in vacuo. The crude residue was dissolved in 1,4-dioxane (8 mL) and 25% aqueous ammonium hydroxide solution (2 mL) was added. The mixture was heated overnight at 110° C. in a sealed vessel, then cooled and extracted using EtOAc and brine. The solvents were evaporated in vacuo. The residue (68 mg, 0.19 mmol) was dissolved in chloroform (2 mL) and trimethylsilyl iodide (96 µL, 0.66 mmol) was added. Progress of the reaction was followed by TLC. After completion, the solution was evaporated, and the residue was dissolved in DCM (4 mL). To a first aliquot (2 mL) of the DCM solution were added DIPEA (155 µL, 0.95 mmol) and Intermediate 25 (33 mg, 0.1 mmol). The reaction mixture was stirred overnight at r.t. The solution was evaporated in vacuo, and the residue was purified by silica gel chromatography (gradient 2-8% MeOH in DCM). The title compound (32 mg, 22% overall) was isolated as a white solid. $^{13}$C NMR (DMSO-d$_6$, 75 MHz) δ 158.0, 156.8, 156.3, 154.5, 152.8, 144.7, 138.3, 137.1, 125.7, 121.4, 117.1 (t, J$_{CF}$ 271.8 Hz), 104.8, 62.1 (2C, t, J$_{CF}$ 25.2 Hz), 51.3, 47.9, 44.1, 43.4, 38.7, 20.9, 14.4, 10.7. MS (m/z) 487 [M+H]+.

Example 15

(3S)-4-(5-Amino-1,3-dimethyl-1H-pyrazolo[4,3-d]pyrimidin-7-yl)-N-(4-methoxy-2-methylphenyl)-3-methylpiperazine-1-carboxamide To a second aliquot (2 mL) of the DCM solution prepared in Example 14 were added DIPEA (155 µL, 0.95 mmol) and 4-methoxy-2-methylphenyl isocyanate (14 µL, 0.1 mmol) at r.t. The solution was evaporated in vacuo, and the residue was purified by silica gel chromatography (gradient 2-8% MeOH in DCM), to give the title compound (25 mg, 20% overall) as a white solid. $^{13}$C NMR (DMSO-d$_6$, 75 MHz) δ 156.9, 156.8, 156.3, 154.5, 143.9, 137.4, 135.7, 130.7, 128.1, 121.2, 115.3, 111.1, 56.0, 51.3, 47.9, 44.2, 43.4, 38.9, 18.2, 14.6, 10.8. MS (m/z) 425 [M+H]+.

Example 16

(3S)-4-(5-Amino-1-methyl-1H-pyrazolo[4,3-d]pyrimidin-7-yl)-N-[6-(3,3-difluoroazetidin-1-yl)-2-methylpyridin-3-yl]-3-methylpiperazine-1-carboxamide Prepared from Intermediate 21 (234 mg, 1.2 mmol) according to the procedure described for Example 14, using Intermediate 25 (163 mg, 0.5 mmol) in the final step. The crude residue was purified by silica gel chromatography (gradient 2-8% MeOH in DCM) to give the title compound (49 mg, 7% overall) as a white solid. $^{13}$C NMR (DMSO-d$_6$, 75 MHz) δ 158.8, 156.8 (t, J$_{CF}$ 2.8 Hz), 156.3, 154.6, 152.8, 147.8, 137.1, 130.4, 125.7, 121.0, 117.1 (t, J$_{CF}$ 271.8 Hz), 104.8, 62.2 (2C, t, J$_{CF}$ 25.4 Hz), 51.4, 48.0, 44.5, 43.3, 38.8, 20.8, 14.4. MS (m/z) 473 [M+H]+.

Example 17

(3S)-4-(5-Amino-1-methyl-1H-pyrazolo[4,3-d]pyrimidin-7-yl)-N-(4-methoxy-2-methylphenyl)-3-methylpiperazine-1-carboxamide Prepared from Intermediate 21 (234 mg, 1.2 mmol) and 4-methoxy-2-methylphenyl isocyanate (69 µL, 0.5 mmol) according to the procedure described for Example 15. The crude residue was purified by silica gel chromatography (gradient 2-8% MeOH in DCM) to give the title compound (45 mg, 9% overall) as a white solid. $^{13}$C NMR (DMSO-d$_6$, 75 MHz) δ 158.9, 156.8, 156.4, 154.7, 147.9, 135.6, 130.8, 130.4, 128.2, 121.1, 115.3, 111.1, 55.2, 51.5, 48.1, 44.5, 43.4, 39.1, 18.2, 14.4. MS (m/z) 411 [M+H]+.

Example 18

(3S)-4-(2-Amino-5-methylpyrrolo[3,2-d]pyrimidin-4-yl)-N-(4-methoxy-2-methylphenyl)-3-methylpiperazine-1-carboxamide Prepared from Intermediate 35 and Intermediate 26 according to the procedure described for Example 10 yielding the title compound (122 mg, 71%) as a white solid. δ$_H$ (400 MHz, DMSO-d$_6$) 8.01 (s, 1H), 7.41 (d, 1H, J 3.0 Hz), 7.03 (d, 1H, J 8.6 Hz), 6.78 (d, 1H, J 2.8 Hz), 6.70 (dd, 1H, J 8.6, 2.9 Hz), 6.11 (d, 1H, J 3.0 Hz), 6.04 (br s, 2H), 3.90 (m, 1H), 3.86 (s, 3H), 3.73-3.79 (m, 1H), 3.72 (s, 3H), 3.59-3.64 (m, 1H), 3.49-3.54 (m, 1H), 3.41-3.48 (m, 1H), 3.33-3.40 (m, 1H), 3.16-3.22 (m, 1H), 2.15 (s, 3H), 1.09 (d, 3H, J 6.4 Hz). LCMS (ES−) [M−H]− 408, RT 1.57 minutes (method 2).

Example 19

(3S)-4-(2-Amino-5-methylpyrrolo[3,2-d]pyrimidin-4-yl)-N-(4-methoxy-3-methylphenyl)-3-methylpiperazine-1-carboxamide Prepared from Intermediate 35 and Intermediate 27 according to the procedure described for Example 10 yielding the title compound (122 mg, 71%) as a white solid. δ$_H$ (400 MHz, DMSO-d$_6$) 8.34 (s, 1H), 7.40 (d, 1H, J 3.0 Hz), 7.20-7.24 (m, 1H), 7.21 (s, 1H), 6.80-6.83 (m, 1H), 6.10 (d, 1H, J 3.0 Hz), 5.94 (br s, 2H), 3.87 (s, 3H), 3.84 (m, 1H), 3.73 (s, 3H), 3.62-3.68 (m, 2H), 3.42-3.54 (m, 2H), 3.31-3.38 (m, 1H), 3.10-3.18 (m, 1H), 2.11 (s, 3H), 1.06 (d, 3H, J 6.3 Hz). LCMS (ES–) [M–H]⁻ 408, RT 1.73 minutes (method 2).

Example 20

(3S)-4-(2-Amino-5-methylpyrrolo[3,2-d]pyrimidin-4-yl)-3-methyl-N-[2-methyl-4-(trifluoromethoxy)phenyl]piperazine-1-carboxamide Prepared from Intermediate 35 and Intermediate 23 (131 mg, 0.42 mmol) according to the procedure described for Example 10 yielding the title compound (183 mg, 93%) as a white solid. $\delta_H$ (400 MHz, DMSO-$d_6$) 8.24 (s, 1H), 7.47 (d, 1H, J 2.9 Hz), 7.29 (m, 1H), 7.20-7.22 (m, 1H), 7.12-7.15 (m, 1H), 6.53 (br s, 2H), 6.17 (d, 1H, J 2.9 Hz), 4.12 (br s, 1H), 3.90 (br s, 1H), 3.86 (s, 3H), 3.65-3.71 (m, 1H), 3.52-3.58 (m, 1H), 3.33-3.49 (m, 3H), 2.22 (s, 3H), 1.17 (d, 3H, J 6.4 Hz). LCMS (ES–) [M–H]⁻ 462, RT 2.09 minutes (method 2).

Example 21

(3S)-4-(5-Amino-3-methylisoxazolo[4,5-d]pyrimidin-7-yl)-3-ethyl-N-(4-methoxy-2-methylphenyl)piperazine-1-carboxamide Prepared from Intermediate 11 and Intermediate 26 according to the procedure described for Example 10 yielding the title compound (73 mg, 50%) as a white solid. $\delta_H$ (400 MHz, DMSO-$d_6$) 8.02 (s, 1H), 7.02 (d, J 8.3 Hz, 1H), 6.78 (d, J 2.45 Hz, 1H), 6.71 (dd, J 8.6, 2.7 Hz, 1H), 6.21 (br s, 2H), 4.48-4.83 (m, 2H), 4.17 (m, 2H), 3.72 (s, 3H), 3.18 (d, J 11.2 Hz, 1H), 3.02 (m, 1H), 2.36 (s, 3H), 2.30 (m, 1H), 2.14 (s, 3H), 1.66-1.82 (m, 2H), 0.87 (t, J 7.4 Hz, 3H). LCMS (ES+) [M+H]⁺ 426.0, RT 2.15 minutes (method 2).

Example 22

(3S)-4-(5-Amino-3-methylisoxazolo[4,5-d]pyrimidin-7-yl)-3-ethyl-N-(4-methoxy-3-methylphenyl)piperazine-1-carboxamide Prepared from Intermediate 11 and Intermediate 27 according to the procedure described for Example 10 yielding the title compound (80 mg, 52%) as a white solid. $\delta_H$ (400 MHz, DMSO-$d_6$) 8.35 (s, 1H) 7.15-7.27 (m, 2H), 6.82 (d, J 9.2 Hz, 1H), 6.21 (br s, 2H), 4.45-4.80 (m, 2H), 4.18 (m, 2H), 3.73 (s, 3H), 3.15 (d, J 11.74 Hz, 1H), 3.03 (d, J 11.25 Hz, 1H), 2.38 (s, 3H), 2.30 (m, 1H), 2.11 (s, 3H), 1.66-1.82 (m, 2H), 0.84 (t, J 7.4 Hz, 3H). LCMS (ES+) [M+H]⁺ 426.0, RT 2.29 minutes (method 2).

Example 23

(3S)-4-(5-Amino-3-methylisoxazolo[4,5-d]pyrimidin-7-yl)-N-[6-(dimethylamino)-2-methylpyridin-3-yl]-3-ethylpiperazine-1-carboxamide Prepared from Intermediate 11 and Intermediate 28 according to the procedure described for Example 10 yielding the title compound (83 mg, 55%) as a white solid. $\delta_H$ (400 MHz, DMSO-$d_6$) 7.99 (s, 1H), 7.21 (d, J 8.3 Hz, 1H), 6.43 (d, J 8.8 Hz, 1H), 6.21 (s, 2H), 4.57-4.80 (m, 3H), 4.16 (m, 2H), 3.17 (m, 2H), 3.10 (m, 1H), 2.99 (s, 6H), 2.36 (s, 3H), 2.21 (s, 3H), 1.66-1.82 (m, 2H), 0.87 (t, J 7.4 Hz, 3H). LCMS (ES+) [M+H]⁺ 440.0, RT 2.07 minutes (method 2).

Example 24

(3S)-4-(5-Amino-3-methylisoxazolo[4,5-d]pyrimidin-7-yl)-N-[6-(azetidin-1-yl)-2-methylpyridin-3-yl]-3-ethylpiperazine-1-carboxamide Prepared from Intermediate 11 and Intermediate 29 according to the procedure described for Example 10 yielding the title compound (78 mg, 45%) as a white solid. $\delta_H$ (400 MHz, DMSO-$d_6$) 8.02 (s, 1H), 7.22 (d, J 8.4 Hz, 1H), 6.22 (s, 2H), 6.16 (d, J 8.4 Hz, 1H), 4.80-4.57 (br s, 2H), 4.11-4.23 (m, 2H), 3.84-3.92 (m, 4H), 3.18 (d, J 12.4 Hz, 2H), 3.03 (d, J 11.0 Hz, 1H), 2.36 (s, 3H), 2.25-2.32 (m, 3H), 2.19 (s, 3H), 1.67-1.78 (m, 2H), 0.87 (t, J 7.4 Hz, 3H). LCMS (ES+) [M+H]⁺ 452.0, RT 1.87 minutes (method 2).

Example 25

(3S)-4-(5-Amino-3-methylisoxazolo[4,5-d]pyrimidin-7-yl)-3-ethyl-N-[5-methoxy-6-(trifluoromethyl)pyridin-2-yl]piperazine-1-carboxamide Prepared from Intermediate 11 and Intermediate 30 according to the procedure described for Example 10 yielding the title compound (92 mg, 50%) as a white solid. $\delta_H$ (400 MHz, DMSO-$d_6$) 9.37 (s, 1H), 7.97 (d, J 9.3 Hz, 1H), 7.80 (d, J 9.4 Hz, 1H), 6.22 (br s, 2H), 4.51-4.81 (m, 2H), 4.24 (m, 2H), 3.89 (s, 3H), 3.16 (d, J 12.0 Hz, 1H), 3.07 (m, 1H), 2.36 (s, 3H), 2.30 (m, 1H), 1.63-1.76 (m, 2H), 0.83 (t, J 7.4 Hz, 3H). LCMS (ES+) [M+H]⁺ 481.0, RT 2.46 minutes (method 2).

Example 26

(3S)-4-(5-Amino-3-methylisoxazolo[4,5-d]pyrimidin-7-yl)-3-ethyl-N-(4-isopropoxy-2-methylphenyl)piperazine-1-carboxamide Prepared from Intermediate 11 and Intermediate 31 according to the procedure described for Example 10 yielding the title compound (88 mg, 58%) as a white solid. $\delta_H$ (400 MHz, DMSO-$d_6$) 8.00 (s, 1H), 6.99 (d, J 8.4 Hz, 1H), 6.75 (d, J 2.6 Hz, 1H), 6.69 (dd, J 8.4, 2.6 Hz, 1H), 6.22 (s, 2H), 4.55 (m, 3H), 4.16 (d, J 13.4 Hz, 2H), 3.18 (m, 1H), 3.03 (m, 1H), 2.36 (s, 3H), 2.30 (m, 1H), 2.12 (s, 3H), 1.65-1.80 (m, 2H), 1.25 (d, J 5.8 Hz, 6H), 0.87 (t, J 7.4 Hz, 3H). LCMS (ES+) [M+H]⁺ 454.0, RT 2.40 minutes (method 2).

Example 27

(3S)-4-(5-Amino-1-methylpyrazolo[4,3-d]pyrimidin-7-yl)-N-(4-methoxy-3-methylphenyl)-3-methylpiperazine-1-carboxamide Prepared from Intermediate 39 and Intermediate 27 according to the procedure described for Example 10 yielding the title compound (69 mg, 36%) as a white solid. $\delta_H$ (400 MHz, DMSO-$d_6$) 8.35 (s, 1H), 7.64 (s, 1H), 7.19-7.25 (m, 2H), 6.81 (d, J 9.2 Hz, 1H), 6.00 (br s, 2H), 4.02-4.15

(m, 1H), 4.01 (s, 3H), 3.85-4.00 (s, 3H), 3.70 (m, 1H), 3.20-3.40 (m, 5H), 2.09 (s, 3H), 1.09 (d, J 6.4 Hz, 3H). LCMS (ES+) [M+H]+ 411.8, RT 1.61 minutes (method 2).

Example 28

(3S)-4-(5-Amino-1-methylpyrazolo[4,3-d]pyrimidin-7-yl)-3-methyl-N-[2-methyl-4-(trifluoromethoxy)phenyl]piperazine-1-carboxamide Prepared from Intermediate 39 and Intermediate 23 according to the procedure described for Example 10 yielding the title compound (111 mg, 51%) as a white solid. $\delta_H$ (400 MHz, DMSO-$d_6$) 8.25 (s, 1H), 7.65 (s, 1H), 7.08-7.32 (m, 3H), 5.99 (br s, 2H), 4.02-4.16 (m, 1H), 4.02 (s, 3H), 3.85-4.00 (m, 1H), 3.25-3.49 (m, 5H), 2.15 (s, 3H), 1.09 (d, J 6.3 Hz, 3H). LCMS (ES+) [M+H]+ 465.8, RT 1.83 minutes (method 2).

Example 29

(3S)-4-(5-Amino-1,3-dimethyl-1H-pyrazolo[4,3-d]pyrimidin-7-yl)-N-(4-methoxy-3-methylphenyl)-3-methylpiperazine-1-carboxamide Prepared from Intermediate 43 and Intermediate 27 according to the procedure described for Example 10 yielding the title compound (160 mg, 23%) as a white solid. LCMS (ES+) [M+H]+ 425, RT 2.04 minutes (method 2).

Example 30

(3S)-4-(5-Amino-1,3-dimethyl-1H-pyrazolo[4,3-d]pyrimidin-7-yl)-N-(2,6-dimethoxypyridin-3-yl)-3-methylpiperazine-1-carboxamide Prepared from Intermediate 43 and Intermediate 24 according to the procedure described for Example 10 yielding the title compound (235 mg, 33%) as a white solid. LCMS (ES+) [M+H]+ 442, RT 1.82 minutes (method 2).

Example 31

(3S)-4-(5-Amino-3-methylisoxazolo[4,5-d]pyrimidin-7-yl)-N-[5-(dimethylamino)-3-methylpyrazin-2-yl]-3-ethylpiperazine-1-carboxamide To a suspension of Intermediate 11 (1.193 mmol, 400 mg) and phenyl N-[5-(dimethylamino)-3-methylpyrazin-2-yl] carbamate (WO 2014/096423) (309.4 mg, 1.193 mmol) in acetonitrile (50 mL) was added DIPEA (0.41 mL, 2.39 mmol). The reaction mixture was left overnight, then concentrated in vacuo. The residue was partitioned between DCM (50 mL) and water (50 mL), then phase separated. The organic layers were concentrated in vacuo, then subject to column chromatography (Isolera, 50 g Si cartridge, eluting with 100% EtOAc to 20% MeOH in EtOAc), to yield the title compound (288 mg, 54.8%) as an off white solid. $\delta_H$ (300 MHz, DMSO-$d_6$) 8.56 (s, 1H), 7.73 (s, 1H), 6.20 (s, 2H), 4.49-4.79 (m, 2H), 4.18 (d, J 13.4 Hz, 1H), 3.04-3.35 (m, 3H), 3.04 (s, 6H), 2.36 (s, 3H), 2.22 (s, 3H), 1.65-1.80 (m, 2H), 0.86 (t, J 7.4 Hz, 3H). LCMS (ES+) [M+H]+ 441, RT 1.57 minutes (method 2).

The invention claimed is:
1. A compound of formula ((IB) or a pharmaceutically acceptable salt or solvate thereof:

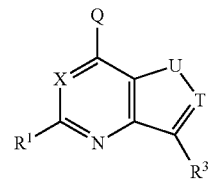

wherein
X represents N;
T represents N;
U represents oxygen or N—$R^4$;
Q represents a group of formula (Qa), (Qb), (Qc), (Qd) or (Qe):

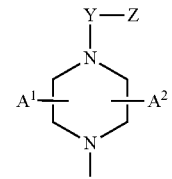

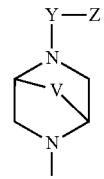

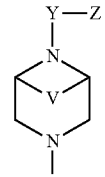

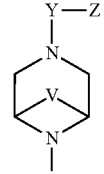

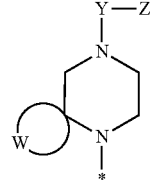

in which the asterisk (*) represents the point of attachment to the remainder of the molecule;

V represents —CH$_2$—, —C(CH$_3$)$_2$—, —CH$_2$CH$_2$— or —CH$_2$CH$_2$CH$_2$—;

W represents the residue of a C$_{3-7}$ cycloalkyl group;

Y represents —C(O)—, —C(O)N(R$^5$)—, OR —C(O)C(O)—;

Z represents aryl or heteroaryl, either of which groups is optionally substituted by one, two, or three substituents independently selected from halogen, cyano, nitro, C$_{1-6}$ alkyl, trifluoromethyl, cyano-(C$_{1-6}$)alkyl, (C$_{3-7}$)heterocycloalkyl, halo(C$_{3-7}$)heterocycloalkyl, (C$_{1-6}$)alkyl(C$_{3-7}$)heterocycloalkyl, (C$_{2-6}$)alkoxycarbonyl(C$_{3-7}$)heterocycloalkyl, dihalo(C$_{3-7}$)heterocycloalkyl, (C$_{3-7}$)heterocycloalkyl(C$_{1-6}$)alkyl, (C$_{1-6}$)alkyl(C$_{3-7}$)heterocycloalkyl(C$_{1-6}$)alkyl, heteroaryl, hydroxy, oxo, C$_{1-6}$ alkoxy, difluoromethoxy, trifluoromethoxy, trifluoroethoxy (C$_{3-7}$)heterocycloalkoxy, (C$_{2-6}$)alkoxycarbonyl(C$_{3-7}$)heterocycloalkoxy, (C$_{3-7}$)heterocycloalkyl(C$_{1-6}$)alkoxy, aryloxy, haloaryloxy, (C$_{1-6}$)alkoxyaryloxy, C$_{1-3}$ alkylenedioxy, dihalo(C$_{1-3}$)alkylenedioxy, arylcarbonyloxy, C$_{1-6}$ alkylthio, C$_{1-6}$ alkylsulfinyl, C$_{1-6}$ alkyl sulfonyl, amino, C$_{1-6}$ alkylamino, di(C$_{1-6}$)alkylamino, di(C$_{1-6}$)alkylamino(C$_{1-6}$)alkyl, arylamino, C$_{2-6}$ alkylcarbonylamino, C$_{2-6}$ alkoxycarbonylamino, C$_{1-6}$ alkylsulfonylamino, formyl, C$_{2-6}$ alkylcarbonyl, C$_{3-6}$ cycloalkylcarbonyl, C$_{3-6}$ heterocycloalkylcarbonyl, carboxy, C$_{2-6}$ alkoxycarbonyl, aryloxycarbonyl, aminocarbonyl, C$_{1-6}$ alkylaminocarbonyl, di(C$_{1-6}$)alkylaminocarbonyl, aminosulfonyl, C$_{1-6}$ alkylaminosulfonyl and di(C$_{1-6}$)alkylaminosulfonyl;

A$^1$ represents hydrogen, cyano or trifluoromethyl; or A$^1$ represents C$_{1-6}$ alkyl, optionally substituted by one or more substituents independently selected from fluoro, —OR$^a$, trifluoromethoxy, —NR$^b$R$^c$, —CO$_2$R$^d$ and —CONR$^b$R$^c$; or A$^1$ represents C$_{3-7}$ cycloalkyl;

A$^2$ represents hydrogen or C$_{1-6}$ alkyl;

R$^1$ represents —NR$^b$R$^c$;

R$^3$ represents hydrogen, halogen or C$_{1-6}$ alkyl;

R$^4$ represents hydrogen; or R$^4$ represents C$_{1-6}$ alkyl, aryl, aryl(C$_{1-6}$)alkyl, heteroaryl or heteroaryl(C$_{1-6}$)alkyl, any of which groups may be optionally substituted by one or more substituents;

R$^5$ represents hydrogen; or R$^5$ represents C$_{1-6}$ alkyl, optionally substituted by one or more substituents independently selected from —OR$^a$ and —NR$^b$R$^c$;

R$^a$ represents hydrogen; or R$^a$ represents C$_{1-6}$ alkyl, aryl, aryl(C$_{1-6}$)alkyl, heteroaryl or heteroaryl(C$_{1-6}$)alkyl, any of which groups may be optionally substituted by one or more substituents;

R$^b$ and R$^c$ independently represent hydrogen or trifluoromethyl; or C$_{1-6}$ alkyl, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted by one or more substituents; or R$^b$ and R$^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents; and R$^d$ represents hydrogen; or C$_{1-6}$ alkyl, C$_{3-7}$ cycloalkyl, aryl, C$_{3-7}$ heterocycloalkyl or heteroaryl, any of which groups may be optionally substituted by one or more substituents.

2. The compound as claimed in claim 1 wherein Q represents a group of formula (Qa-1), (Qa-2) or (Qa-3):

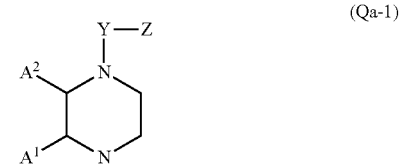

(Qa-1)

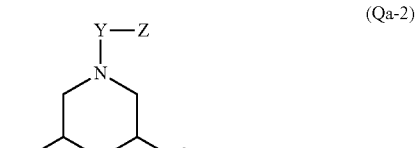

(Qa-2)

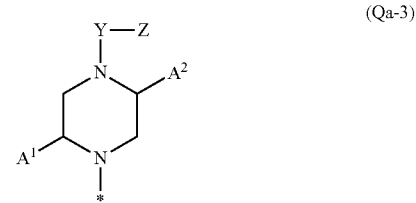

(Qa-3)

in which the asterisk (*) represents the point of attachment to the remainder of the molecule.

3. The compound as claimed in claim 1 represented by formula (IIB-1), or a pharmaceutically acceptable salt or solvate thereof:

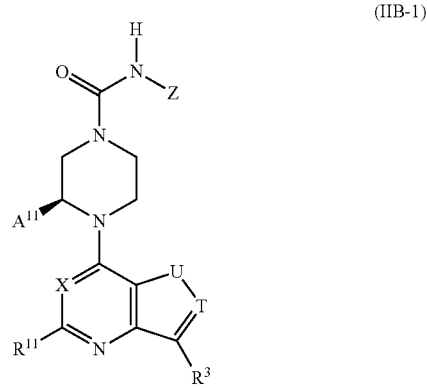

(IIB-1)

wherein

A$^{11}$ represents hydrogen, cyano, C$_{1-6}$ alkyl, —CH$_2$OR$^a$, —CH$_2$CH$_2$OR$^a$, —CH$_2$CO$_2$R$^d$, —CH$_2$CONR$^b$R$^c$ or C$_{3-7}$ cycloalkyl; and R$^{11}$ represents amino.

4. The compound as claimed in claim 1 represented by formula (IIB-2), or a pharmaceutically acceptable salt or solvate thereof:

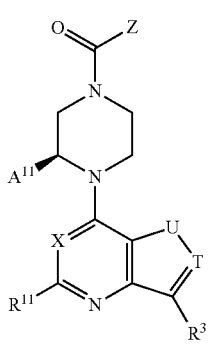

(IIB-2)

A[11] represents hydrogen, cyano, $C_{1-6}$ alkyl, —$CH_2OR^a$, —$CH_2CH_2OR^a$, —$CH_2CO_2R^d$, —$CH_2CONR^bR^c$ or $C_{3-7}$ cycloalkyl; and R[11] represents amino.

5. The compound as claimed in claim 3 wherein A[11] represents hydrogen or $C_{1-6}$ alkyl.

6. The compound as claimed in claim 5 wherein A[11] represents hydrogen, methyl or ethyl.

7. The compound as claimed in claim 1 wherein Z represents aryl or heteroaryl, either of which groups may be optionally substituted by one, two or three substituents independently selected from $C_{1-6}$ alkyl, trifluoromethyl, $(C_{3-7})$heterocycloalkyl, dihalo$(C_{3-7})$heterocycloalkyl, $C_{1-6}$ alkoxy, trifluoromethoxy and di$(C_{1-6})$alkylamino.

8. The compound as claimed in claim 7 wherein Z represents methoxyphenyl, dimethylaminophenyl, (methoxy)(methyl)phenyl, (isopropoxy)(methyl)phenyl, (methyl)(trifluoromethoxy)phenyl, (azetidinyl)(methyl)pyridinyl, (difluoroazetidinyl)-(methyl)pyridinyl, (methoxy)(trifluoromethyl)pyridinyl, dimethoxypyridinyl, (ethoxy)-(methyl)pyridinyl or (dimethylamino)(methyl)pyridinyl.

9. The compound as claimed in claim 1 wherein $R^3$ represents hydrogen or methyl.

10. The compound of formula ((IB) as defined in claim 1 which is (3S)-4-(5-Amino-3-methyl[1,2]oxazolo[4,5-d]pyrimidin-7-yl)-N-(6-ethoxy-2-methylpyridin-3-yl)-3-ethylpiperazine-1-carboxamide, (3S)-4-(5-Amino-3-methyl[1,2]oxazolo[4,5-d]pyrimidin-7-yl)-3-ethyl-N-[2-methyl-4-(trifluoromethoxy)phenyl]piperazine-1-carboxamide, (3S)-4-(5-Amino-3-methyl[1,2]oxazolo[4,5-d]pyrimidin-7-yl)-N-(2,6-dimethoxypyridin-3-yl)-3-ethylpiperazine-1-carboxamide, (3S)-4-(5-Amino-1,3-dimethyl-1H-pyrazolo[4,3-d]pyrimidin-7-yl)-N-[6-(3,3-difluoroazetidin-1-yl)-2-methylpyridin-3-yl]-3-methylpiperazine-1-carboxamide, (3S)-4-(5-Amino-1,3-dimethyl-1H-pyrazolo[4,3-d]pyrimidin-7-yl)-N-(4-methoxy-2-methylphenyl)-3-methylpiperazine-1-carboxamide, (3S)-4-(5-Amino-1-methyl-1H-pyrazolo[4,3-d]pyrimidin-7-yl)-N-[6-(3,3-difluoroazetidin-1-yl)-2-methylpyridin-3-yl]-3-methylpiperazine-1-carboxamide, (3S)-4-(5-Amino-1-methyl-1H-pyrazolo[4,3-d]pyrimidin-7-yl)-N-(4-methoxy-2-methylphenyl)-3-methylpiperazine-1-carboxamide, (3S)-4-(2-Amino-5-methylpyrrolo[3,2-d]pyrimidin-4-yl)-3-methyl-N-[2-methyl-4-(trifluoromethoxy)phenyl]piperazine-1-carboxamide, (3S)-4-(5-Amino-3-methylisoxazolo[4,5-d]pyrimidin-7-yl)-3-ethyl-N-(4-methoxy-2-methylphenyl)piperazine-1-carboxamide, (3S)-4-(5-Amino-3-methylisoxazolo[4,5-d]pyrimidin-7-yl)-3-ethyl-N-(4-methoxy-3-methylphenyl)piperazine-1-carboxamide, (3S)-4-(5-Amino-3-methylisoxazolo[4,5-d]pyrimidin-7-yl)-N-[6-(dimethylamino)-2-methylpyridin-3-yl]-3-ethylpiperazine-1-carboxamide, (3S)-4-(5-Amino-3-methylisoxazolo[4,5-d]pyrimidin-7-yl)-N-[6-(azetidin-1-yl)-2-methyl-pyridin-3-yl]-3-ethylpiperazine-1-carboxamide, (3S)-4-(5-Amino-3-methylisoxazolo[4,5-d]pyrimidin-7-yl)-3-ethyl-N-[5-methoxy-6-(trifluoromethyl)pyridin-2-yl]piperazine-1-carboxamide, (3S)-4-(5-Amino-3-methylisoxazolo[4,5-d]pyrimidin-7-yl)-3-ethyl-N-(4-isopropoxy-2-methylphenyl)piperazine-1-carboxamide, (3S)-4-(5-Amino-1-methylpyrazolo[4,3-d]pyrimidin-7-yl)-N-(4-methoxy-3-methylphenyl)-3-methylpiperazine-1-carboxamide, (3S)-4-(5-Amino-1-methylpyrazolo[4,3-d]pyrimidin-7-yl)-3-methyl-N-[2-methyl-4-(trifluoromethoxy)phenyl]piperazine-1-carboxamide, (3S)-4-(5-Amino-1,3-dimethyl-1H-pyrazolo[4, 3-d]pyrimidin-7-yl)-N-(4-methoxy-3-methylphenyl)-3-methylpiperazine-1-carboxamide, (3S)-4-(5-Amino-1,3-dimethyl-1H-pyrazolo[4,3-d]pyrimidin-7-yl)-N-(2,6-dimethoxypyridin-3-yl)-3-methylpiperazine-1-carboxamide, or (3S)-4-(5-Amino-3-methylisoxazolo[4,5-d]pyrimidin-7-yl)-N-[5-(dimethylamino)-3-methylpyrazin-2-yl]-3-ethylpiperazine-1-carboxamide.

11. A pharmaceutical composition comprising a compound of formula ((IB) as defined in claim 1 or a pharmaceutically acceptable salt or solvate thereof, in association with a pharmaceutically acceptable carrier.

12. A method for the treatment of malaria or the management of organ or cell transplant rejection, which comprises administering to a patient in need of such treatment an effective amount of a compound of formula ((IB) as defined in claim 1 or a pharmaceutically acceptable salt or solvate thereof.

* * * * *